United States Patent [19]

Namekawa et al.

[11] Patent Number: 5,595,684
[45] Date of Patent: Jan. 21, 1997

[54] OPTICALLY ACTIVE TETRAHYDROPYRAN DERIVATIVE, LIQUID CRYSTAL COMPOSITION, AND LIQUID CRYSTAL DEVICE CONTAINING THE SAME

[75] Inventors: Masaaki Namekawa; Keizou Itoh; Shinichi Nayuki; Mitsunori Takeda; Yoshinobu Murayama, all of Ibaraki-ken, Japan

[73] Assignee: Kashima Oil Company, Tokyo, Japan

[21] Appl. No.: 415,676

[22] Filed: Apr. 3, 1995

[30] Foreign Application Priority Data

Apr. 11, 1994 [JP] Japan .................... 6-071913

[51] Int. Cl.$^6$ .................... C09K 19/34; G02F 1/13; C07D 309/00; C07F 7/04
[52] U.S. Cl. .................... 252/299.61; 252/299.01; 549/356; 549/416; 556/445; 556/482; 556/489; 349/182
[58] Field of Search .................... 252/299.61, 299.01; 359/103; 549/356, 416; 556/445, 482, 489

[56] References Cited

U.S. PATENT DOCUMENTS

| | | |
|---|---|---|
| 5,296,616 | 3/1994 | Namekawa et al. |
| 5,368,771 | 11/1994 | Namekawa et al. |
| 5,437,814 | 8/1995 | Koden et al. .................... 252/299.61 |
| 5,443,755 | 8/1995 | Namekawa et al. .................... 252/299.61 |

FOREIGN PATENT DOCUMENTS

| | | |
|---|---|---|
| 0594861 | 5/1994 | European Pat. Off. |
| 0622441 | 11/1994 | European Pat. Off. |

OTHER PUBLICATIONS

CA 119:203295, 1993.
CA 123:242632, 1995.

*Primary Examiner*—Shean C. Wu
*Attorney, Agent, or Firm*— Oblon, Spivak, McClelland, Maier & Neustadt, P.C.

[57] ABSTRACT

An optically active tetrahydropyran derivative represented by one of the following general formulae, a liquid crystal composition containing the derivative, and a liquid crystal device containing the composition are disclosed. The optically active tetrahydropyran derivative is a novel compound which is chemically stable, causes no coloring, has excellent optical stability, and shows a large spontaneous polarization and a quick response. The optically active tetrahydropyran derivative can show a more excellent quick response when it is used in a composition, and is useful as a component in a ferroelectric liquid crystal which induces a large spontaneous polarization.

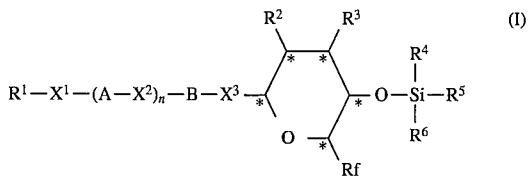

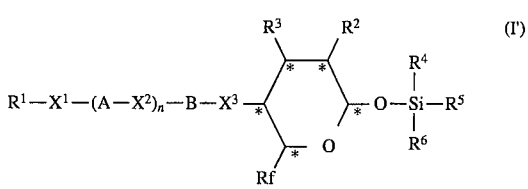

6 Claims, No Drawings

OPTICALLY ACTIVE TETRAHYDROPYRAN DERIVATIVE, LIQUID CRYSTAL COMPOSITION, AND LIQUID CRYSTAL DEVICE CONTAINING THE SAME

BACKGROUND OF THE INVENTION

1. Field of the Invention

The present invention relates to an optically active tetrahydropyran derivative, a liquid crystal composition containing the derivative, and a liquid crystal device containing the composition. More particularly, the present invention relates to a novel optically active tetrahydropyran derivative useful as a liquid crystal material used for a display device or an electro-optical device, a liquid crystal composition containing the derivative, and a liquid crystal device containing the composition.

2. Description of the Related Arts

In recent years, fields for application of liquid crystals, such as various kinds of display devices, electronic optical devices, liquid crystal sensors, and the like, have been expanding remarkably, and liquid crystal compounds having various structures have been proposed in parallel with this expansion of the field. Particularly, nematic liquid crystals are mainly used at present as the liquid crystal material for display devices. The nematic liquid crystals are used in a TN type or STN type simple matrix system and a TFT type active matrix system in which a thin film transistor is provided to each picture element. However, driving force of the nematic liquid crystal is based on a weak interaction between anisotropy of a dielectric constant of a liquid crystal material and an electric field. Therefore, the nematic liquid crystal has a drawback in that the response time is essentially low (of the order of msec). Thus, the nematic liquid crystal is disadvantageous as a material for a display device of a large area to which the high speed response is required.

In contrast, a ferroelectric liquid crystal which was first synthesized by R. B. Meyer et al. in 1975 has a spontaneous polarization, and this liquid crystal has a large driving force because this liquid crystal interacts directly with an electric field. Since N. A. Clark et al. reported in 1980 that a surface stabilized ferroelectric liquid crystal device (SSFLCD) has a high speed response of the order of micro-second and a memory effect, the ferroelectric liquid crystal has been attracting attention, and many ferroelectric liquid crystal compounds have been synthesized.

It is well known that the response time of a ferroelectric liquid crystal is expressed by the equation: $\tau=\eta/(Ps \cdot E)$. Herein, $\eta$ represents rotational viscosity, Ps represents spontaneous polarization, and E represents intensity of an electric field. Based on this equation, a liquid crystal material having a lower viscosity and a larger spontaneous polarization has been the target of the development to achieve a high speed response. As a material for a liquid crystal, properties such as chemical stability and a wide working temperature range are required. However, it is difficult to satisfy all the requirements with a single compound. Accordingly, a method of mixing several types of compound having a chiral smectic C phase (SmC* phase), or a method of adding an optically active compound to an achiral host liquid crystal having a smectic C phase (SmC phase) of a low viscosity, was adopted to obtain a ferroelectric liquid crystal composition having desired characteristics and exhibiting the SmC* phase.

In the latter method, the chiral dopant to be added may have or need not have a SmC* phase by itself, but it is required that the chiral dopant has a good compatibility with the achiral host liquid crystal, induces a high magnitude of spontaneous polarization, and does not cause increase in the viscosity.

The spontaneous polarization is considered to arise as the result of restriction of the free rotation of a dipole moment perpendicular to the long axis of the molecule around the long axis of the molecule by the effect of an asymmetric carbon. Accordingly, many attempts to increase spontaneous polarization have been made by such methods as (1) placing a dipole portion at a position close to a skeleton portion which is a so-called core, (2) placing a dipole portion and an asymmetric carbon at positions close to each other, and (3) attaching a sterically large substituent to an asymmetric carbon, and thereby restricting the free rotation around the molecular axis. Further, it has recently been reported that a compound having a structure in which a dipole portion and an asymmetric carbon are directly bonded to a five-membered lactone shows effective restriction of the free rotation and has a large spontaneous polarization (Japanese Journal of Applied Physics, Volume 29, No. 6, ppL 981 to L 983).

SUMMARY OF THE INVENTION

Under such circumstances, the present inventors have intensively studied with the object to develop a novel optically active compound having tetrahydropyran ring which is useful as a novel type of liquid crystal, has a large spontaneous polarization, and exhibits excellent high speed response.

As the result of the studies, it was discovered that a novel compound in which a tetrahydropyran ring has an asymmetric carbon atom having a fluoroalkyl group which itself has a large electron attracting property and another asymmetric carbon atom having a siloxy group, exhibits the liquid crystal property by itself, or can be used as an excellent chiral dopant to form a composition from which a high speed response can be expected, even when the compound does not show the liquid crystal property by itself. The present invention has been completed on the basis of the discovery.

Thus, the present invention provides an optically active tetrahydropyran derivative represented by general formula (I) or (I'):

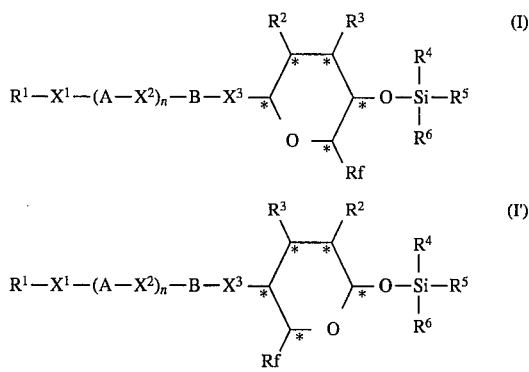

wherein Rf represents a fluoroalkyl group having 1 or 2 carbon atoms; $R^1$ represents a linear or branched alkyl group having 3 to 20 carbon atoms; $R^2$ and $R^3$ each independently represent a hydrogen atom, a linear or branched alkyl group having 1 to 15 carbon atoms, an alkenyl group having 2 to 15 carbon atoms, or an aralkyl group having 7 to 10 carbon atoms; $R^4$, $R^5$, and $R^6$ each independently represent a hydrogen atom, a linear or branched alkyl group having 1 to 15 carbon atoms, an alkenyl group having 2 to 15 carbon atoms, an aryl group having 6 to 10 carbon atoms, or an aralkyl group having 7 to 10 carbon atoms; $X^1$ represents —COO—, —OCO—, —O—, or a single bond; $X^2$ represents —COO—, —OCO—, —CH$_2$O—, —OCH$_2$—, —C≡C—, or a single bond; $X^3$ represents —COO—, —CH$_2$O—, or —O—; Si represents a silicon atom; * shows that the carbon atom having this mark is an asymmetric carbon atom; A and B each independently represent a substituted or unsubstituted group containing a six-membered ring; and n represents 0 or 1.

The present invention also provides a liquid crystal composition containing the optically active tetrahydropyran derivative, and a liquid crystal device comprising the liquid crystal composition.

DESCRIPTION OF PREFERRED EMBODIMENTS

In general formulae (I) and (I'), Rf described above represents a fluoroalkyl group having 1 or 2 carbon atoms. More specifically, Rf represents trifluoromethyl group, difluoromethyl group, chlorodifluoromethyl group, or pentafluoroethyl group, and preferably trifluoromethyl group.

$R^1$ represents a linear or branched alkyl group having 3 to 20 carbon atoms. Examples thereof include n-propyl group, isopropyl group, n-butyl group, isobutyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, and the like. Among these alkyl groups, linear or branched alkyl groups having 3 to 15 carbon atoms are preferable, and linear or branched alkyl groups having 3 to 10 carbon atoms are more preferable. Among these alkyl group, branched alkyl groups having an asymmetric carbon atom are optically active groups.

$R^2$ and $R^3$ each independently represent a hydrogen atom, a linear or branched alkyl group having 1 to 15 carbon atoms, an alkenyl group having 2 to 15 carbon atoms, or an aralkyl group having 7 to 10 carbon atoms. Examples of the linear or branched alkyl group having 1 to 15 carbon atoms include methyl group, ethyl group, n-propyl group, isopropyl group, n-butyl group, sec-butyl group, tert-butyl group, n-pentyl group, isopentyl group, 1-methylbutyl group, n-hexyl group, n-heptyl group, 1-methylheptyl group, n-octyl group, 1-ethylheptyl group, 1-methyloctyl group, n-nonyl group, 1-ethyloctyl group, 1-methylnonyl group, n-decyl group, n-undecyl group, n-dodecyl group, n-tridecyl group, n-tetradecyl group, n-pentadecyl group, and the like. Examples of the alkenyl group having 2 to 15 carbon atoms include vinyl group, allyl group, 1-propenyl group, isopropenyl group, 1-butenyl group, 2-butenyl group, 2-methylallyl group, 1-pentenyl group, 1-hexenyl group, 1-heptenyl group, 1-octenyl group, 2-octenyl group, 1-nonenyl group, 2-nonenyl group, 1-decenyl group, 2-decenyl group, 1-undecenyl group, 2-undecenyl group, 1-dodecenyl group, 2-dodecenyl group, 1-tridecenyl group, 2-tridecenyl group, 1-tetradecenyl group, 2-tetradecenyl group, 1-pentadecenyl group, 2-pentadecenyl group, and the like. Examples of the aralkyl group having 7 to 10 carbon atoms include benzyl group, phenetyl group, phenylpropyl group, phenylbutyl group, and the like.

$R^4$, $R^5$, and $R^6$ each independently represent a hydrogen atom, a linear or branched alkyl group having 1 to 15 carbon atoms, an alkenyl group having 2 to 15 carbon atoms, an aryl group having 6 to 10 carbon atoms, or an aralkyl group having 7 to 10 carbon atoms. Examples of the linear or branched alkyl group having 1 to 15 carbon atoms include methyl group, ethyl group, n-propyl group, isopropyl group, n-butyl group, sec-butyl group, tert-butyl group, n-pentyl group, isopentyl group, 1-methylbutyl group, n-hexyl group, n-heptyl group, 1-methylheptyl group, n-octyl group, 1-ethylheptyl group, 1-methyloctyl group, n-nonyl group, 1-ethyloctyl group, 1-methylnonyl group, n-decyl group, n-undecyl group, n-dodecyl group, n-tridecyl group, n-tetradecyl group, n-pentadecyl group, and the like. Examples of the alkenyl group having 2 to 15 carbon atoms include vinyl group, allyl group, 1-propenyl group, isopropenyl group, 1-butenyl group, 2-butenyl group, 2-methylallyl group, 1-pentenyl group, 1-hexenyl group, 1-heptenyl group, 1-octenyl group, 2-octenyl group, 1-nonenyl group, 2-nonenyl group, 1-decenyl group, 2-decenyl group, 1-undecenyl group, 2-undecenyl group, 1-dodecenyl group, 2-dodecenyl group, 1-tridecenyl group, 2-tridecenyl group, 1-tetradecenyl group, 2-tetradecenyl group, 1-pentadecenyl group, 2-pentadecenyl group, and the like. Examples of the aryl group having 6 to 10 carbon atoms include phenyl group, toluyl group, para-fluorophenyl group, meta-fluorophenyl group, ortho-fluorophenyl group, parachlorophenyl group, meta-chlorophenyl group, ortho-chlorophenyl group, para-trifluormethylphenyl group, para-tert-butylphenyl group, and the like. Examples of the aralkyl group having 7 to 10 carbon atoms include benzyl group, phenetyl group, phenylpropyl group, phenylbutyl group, and the like.

As $R^4$, $R^5$, and $R^6$, linear or branched lower alkyl groups, such as linear or branched alkyl groups having 1 to 10 carbon atoms, are preferable, and linear or branched alkyl groups having 1 to 6 carbon atoms are more preferable among the groups described above.

In general formulae (I) and (I'), A and B each independently represent a substituted or unsubstituted group containing a six-membered ring. Examples of the group containing a six-membered ring include:

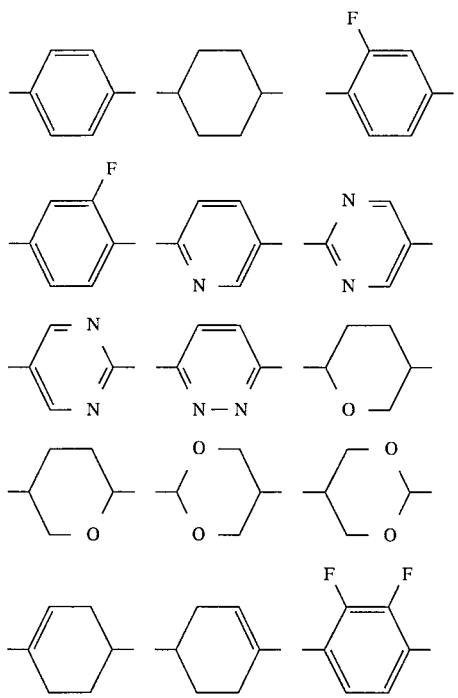

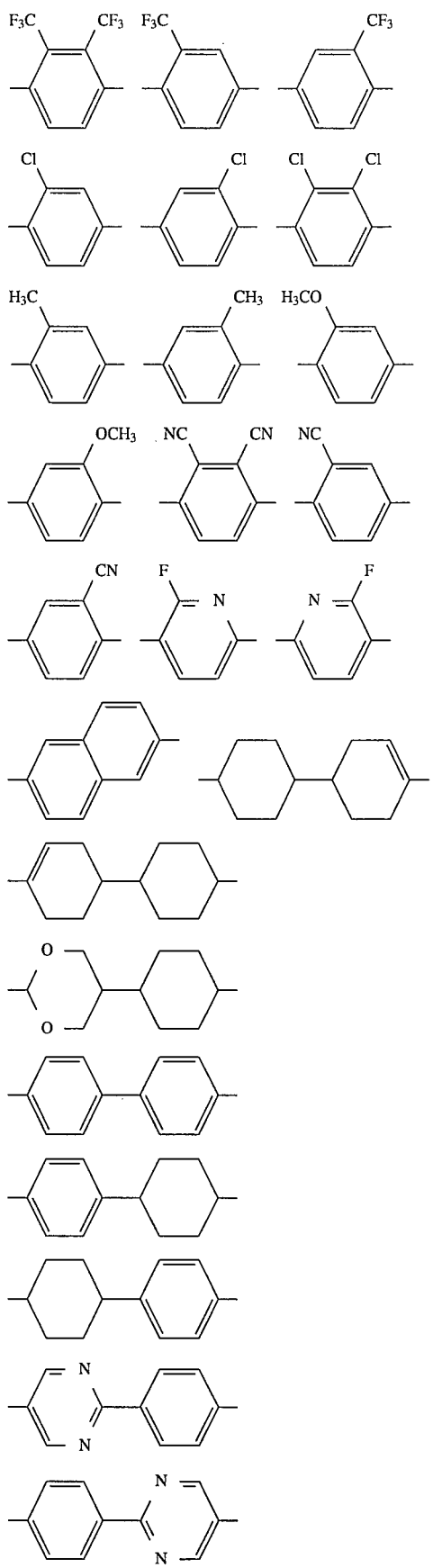

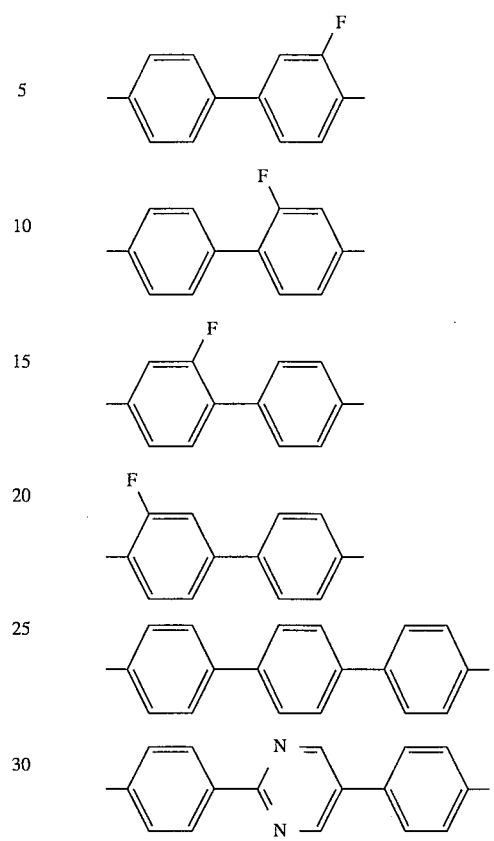

The compound represented by general formula (I) of the present invention can be produced by various methods. For example, the compound represented by general formula (I) can be produced according to the following methods.

(1) A compound represented by the formula (I) in which $X^3$=—COO— and n=0

By bringing a compound represented by the following general formula (II):

[wherein $R^1$, $X^1$, and B are the same as those described above, and Hal represents a halogen, such as chlorine, bromine, and iodine] into reaction with a compound represented by the following general formula (III):

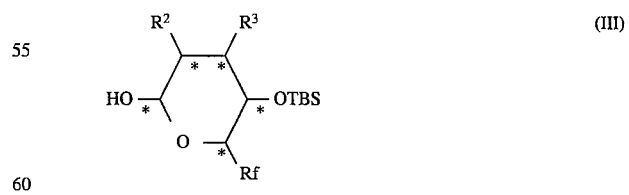

[wherein Rf, $R^2$, $R^3$, and * are the same as those described above, and TBS represents t-butyldimethylsilyl group], a compound represented by the following general formula (IV):

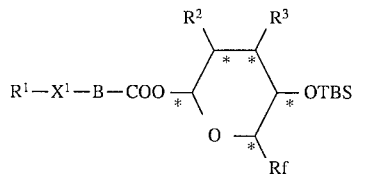

(IV)

[wherein Rf, $R^1$, $R^2$, $R^3$, B, $X^1$, TBS, and * are the same as those described above] can be obtained. This reaction can be conducted in the presence of an organic base, such as pyridine, triethylamine, or the like, in a solvent, such as toluene, benzene, methylene chloride, or the like, in a temperature range from $-20°$ to $80°$ C.

Then, the silyl group is eliminated from the compound represented by general formula (IV) obtained above, and a compound represented by the following general formula (V):

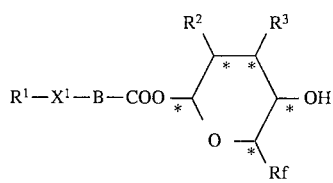

(V)

[wherein Rf, $R^1$, $R^2$, $R^3$, B, $X^1$, TBS, and * are the same as those described above] can be obtained. The reaction of elimination of the silyl group can be conducted according to various methods. For example, the elimination reaction can be conducted in tetrahydrofuran as the solvent, by using tetra-n-butylammonium fluoride as the catalyst, in a temperature range from $0°$ to $50°$ C.

The compound represented by general formula (V) obtained above is a mixture of two diastereomers. The diastereomers can be easily separated by the silica gel column chromatography.

By bringing the compound represented by general formula (V) into reaction with a compound represented by the following general formula (VI):

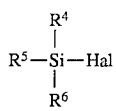

(VI)

[wherein $R^4$, $R^5$, $R^6$, Si, and Hal, are the same as those described above], the target compound represented by general formula (I) can be obtained. This reaction can be conducted in the presence of an organic base, such as imidazole or the like, in a solvent, such as methylene chloride, diethyl ether, tetrahydrofuran, toluene, or the like, in a temperature range from $-20°$ to $120°$ C.

(2) A compound represented by general formula (I) in which $X^3$=—$CH_2O$— and n=0

By bringing a compound represented by the following general formula (VII):

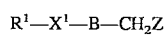

[wherein $R^1$, $X^1$, and B are the same as those described above, and Z represents chlorine, bromine, iodine, or tosyl group] into reaction with the compound represented by general formula (III) described above, a compound represented by the following general formula (VIII):

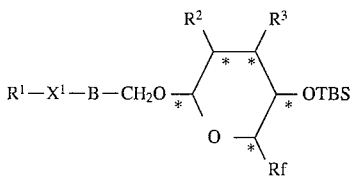

(VIII)

[wherein Rf, $R^1$, $R^2$, $R^3$, $X^1$, B, TBS, and * are the same as those described above] can be obtained. This reaction can be conducted, for example, by using para-toluenesulfonic acid, hydrochloric acid, sulfuric acid, or the like, as the acid catalyst, in a solvent, such as tetrahydrofuran, diethyl ether, methylene chloride, toluene, or the like, in a temperature range from $0°$ to $100°$ C.

Then, the silyl group is eliminated from the compound represented by general formula (VIII), and a compound represented by the following general formula (IX):

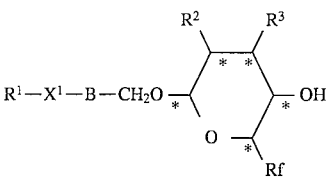

(IX)

[wherein Rf, $R^1$, $R^2$, $R^3$, $X^1$, B, and * are the same as those described above] can be obtained. This reaction of elimination of the silyl group can be conducted by various methods, for example, in tetrahydrofuran as the solvent, by using tetra-n-butylammonium fluoride as the catalyst, in a temperature range from $0°$ to $50°$ C.

The compound represented by general formula (IX) obtained above is a mixture of two diastereomers. The diastereomers can be easily separated by the silica gel column chromatography.

By the reaction of the compound represented by general formula (IX) and the compound represented by general formula (VI) described above, the target compound represented by general formula (I) can be obtained. This reaction can be conducted in the presence of an organic base, such as imidazole or the like, in a solvent, such as methylene chloride, diethyl ether, tetrahydrofuran, toluene, or the like, in a temperature range from $-20°$ to $120°$ C.

(3) A compound represented by general formula (I) in which $X^2$=—COO—, $X^3$=—COO— and n=1

By bringing a compound represented by the following general formula (X):

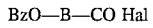

(X)

[wherein B and Hal are the same as those described above, and Bz represents benzyl group] into reaction with the compound represented by general formula (III) described above, a compound represented by the following general formula (XI):

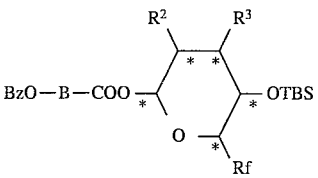

(XI)

[wherein Rf, $R^2$, $R^3$, Bz, B, TBS, and * are the same as those described above] can be obtained. This reaction can be conducted in the presence of an organic base, such as pyridine, triethylamine, or the like, in a solvent, such as toluene, benzene, methylene chloride, or the like, in a temperature range from −20° to 80° C.

Then, the silyl group is eliminated from the compound represented by general formula (XI), and a compound represented by the following general formula (XII):

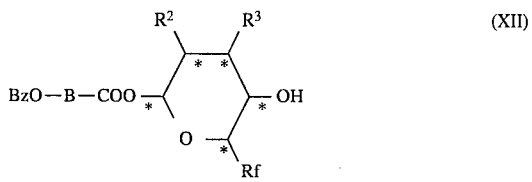

[wherein Rf, R², R³, Bz, B, and * are the same as those described above] can be obtained. This reaction of elimination of the silyl group can be conducted by various methods, for example, in tetrahydrofuran as the solvent, by using tetra-n-butylammonium fluoride as the catalyst, in a temperature range from 0° to 50° C.

By the reaction of the compound represented by general formula (XII) and the compound represented by general formula (VI) described above, a compound represented by the following general formula (XIII):

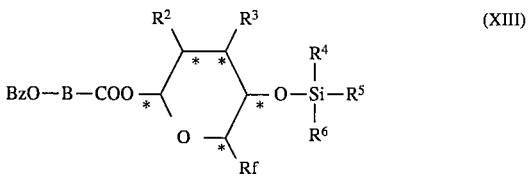

[wherein Rf, R², R³, R⁴, R⁵, R⁶, Bz, B, Si, and * are the same as those described above] can be obtained. This reaction can be conducted in the presence of an organic base, such as imidazole or the like, in a solvent, such as methylene chloride, diethyl ether, tetrahydrofuran, toluene, or the like, in a temperature range from −20° to 120° C.

Then, the benzyl group is eliminated from the compound represented by general formula (XIII) obtained above, and a compound represented by the following general formula (XIV):

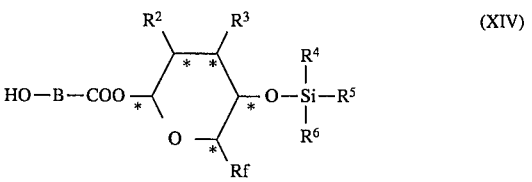

[wherein Rf, R², R³, R⁴, R⁵, R⁶, B, Si, and * are the same as those described above] can be obtained. The reaction of elimination of the benzyl group can be conducted by various methods, for example, the reaction can be conducted by decomposition with hydrogenation at an atmospheric pressure in the presence of a palladium carbon (Pd/C) catalyst by using an alcohol solvent, such as methanol, ethanol, propanol, or the like, or acetic acid.

By bringing the compound represented by general formula (XIV) obtained above into reaction with a compound represented by the following general formula (XV):

R¹—X¹—A—CO Hal        (XV)

[wherein R¹, X¹, A, and Hal are the same as those described above], the target compound represented by general formula (I) can be obtained. This reaction can be conducted, for example, in the presence of an organic base, such as pyridine, triethylamine, or the like, in a solvent, such as toluene, benzene, methylene chloride, or the like, in a temperature range from −20° to 80° C.

The compound represented by general formula (I') of the present invention can be produced by various methods. For example, the compound represented by general formula (I') can be produced according to the following methods.

[1] A compound represented by general formula (I') in which X³=—COO— and n=0

By bringing the compound represented by general formula (III) into reaction with dihydropyran, a compound represented by the following general formula (XVI):

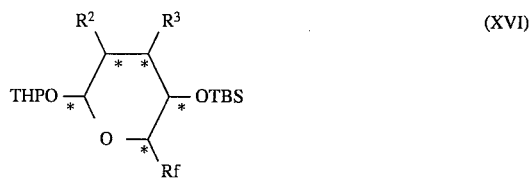

[wherein Rf, R², R³, TBS, and * are the same as those described above, and THP represents tetrahydropyranyl group] can be obtained. This reaction can be conducted by using hydrochloric acid, sulfuric acid, para-toluenesulfonic acid, or the like, as the catalyst, in a solvent, such as diethyl ether, tetrahydrofuran, chloroform, or the like.

Then, the silyl group is eliminated from the compound represented by general formula (XVI) obtained above, and a compound represented by the following general formula (XVII):

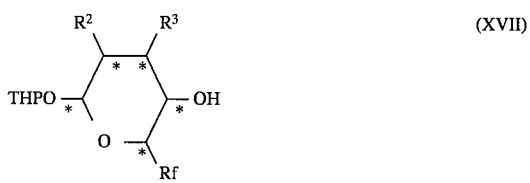

[wherein Rf, R², R³, THP, and * are the same as those described above] can be obtained. The reaction of elimination of the silyl group can be conducted by various methods. For example, the reaction can be conducted in tetrahydrofuran as the solvent, by using tetra-n-butylammonium fluoride as the catalyst, in a temperature range from 0° to 50° C.

By the reaction of the compound represented by general formula (XVII) obtained above and the compound represented by general formula (II) described above, a compound represented by general formula (XVIII):

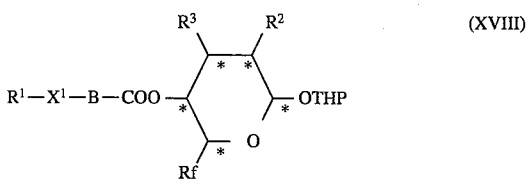

[wherein Rf, R¹, R², R³, B, X¹, THP, and * are the same as those described above] can be obtained. This reaction can be conducted in the presence of an organic base, such as pyridine, triethylamine, or the like, in a solvent, such as toluene, benzene, methylene chloride, or the like, in a temperature range from −20° to 80° C.

Then, THP in the compound represented by general formula (XVIII) is eliminated by a conventional method and a compound represented by the following general formula (XIX):

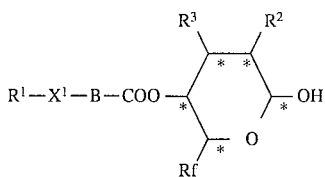

(XIX)

[wherein Rf, $R^1$, $R^2$, $R^3$, B, $X^1$, and * are the same as those described above] is obtained. The elimination of the tetrahydropyranyl group can be conducted in the presence of an acid catalyst, such as hydrochloric acid, sulfuric acid, para-toluenesulfonic acid, or the like, in a solvent, such as diethyl ether, tetrahydrofuran, chloroform, or the like.

By bringing the compound represented by general formula (XIX) obtained above into reaction with the compound represented by general formula (VI) described above, the target compound represented by general formula (I') can be obtained. This reaction can be conducted in the presence of an organic base, such as imidazole or the like, in a solvent, such as methylene chloride, diethyl ether, tetrahydrofuran, toluene, or the like, in a temperature range from $-20°$ to $120°$ C.

[2] A compound represented by general formula (I') in which $X^3=$—$CH_2O$— and n=0

By the reaction of the compound represented by general formula (XVII) described above and the compound represented by general formula (VII) described above, a compound represented by the following general formula (XX):

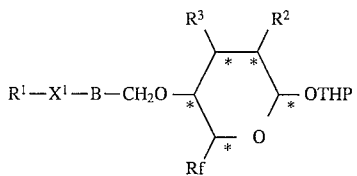

(XX)

[wherein Rf, $R^1$, $R^2$, $R^3$, B, $X^1$, THP, and * are the same as those described above] is obtained. This reaction can be conducted by bringing the compound represented by general formula (XVII) into reaction with a base represented by alkali metal hydride, sodium hydroxide, or potassium hydroxide, and then adding the compound represented by general formula (VII) to the reaction product.

Then, THP in the compound represented by general formula (XX) obtained above is eliminated by a conventional method, and a compound represented by the following general formula (XXI):

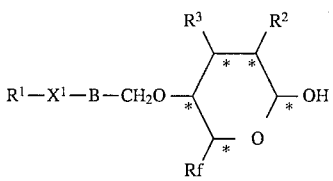

(XXI)

[wherein Rf, $R^1$, $R^2$, $R^3$, B, $X^1$, and * are the same as those described above] is obtained. The reaction of elimination of the tetrahydropyranyl group can be conducted in the presence of an acid catalyst, such as hydrochloric acid, sulfuric acid, para-toluenesulfonic acid, or the like, in a solvent, such as diethyl ether, tetrahydrofuran, chloroform, or the like.

By bringing the compound represented by general formula (XXI) into reaction with the compound represented by general formula (VI) described above, the target compound represented by general formula (I') can be obtained. This reaction can be conducted in the presence of an organic base, such as imidazole or the like, in a solvent, such as methylene chloride, diethyl ether, tetrahydrofuran, toluene, or the like, in a temperature range from $-20°$ to $120°$ C.

The compound represented by general formula (III) which is used as a material for the production of the compound represented by general formula (I) or (I') of the present invention, can be produced by various methods. Representative examples of the compound represented by general formula (III) include the following compounds:

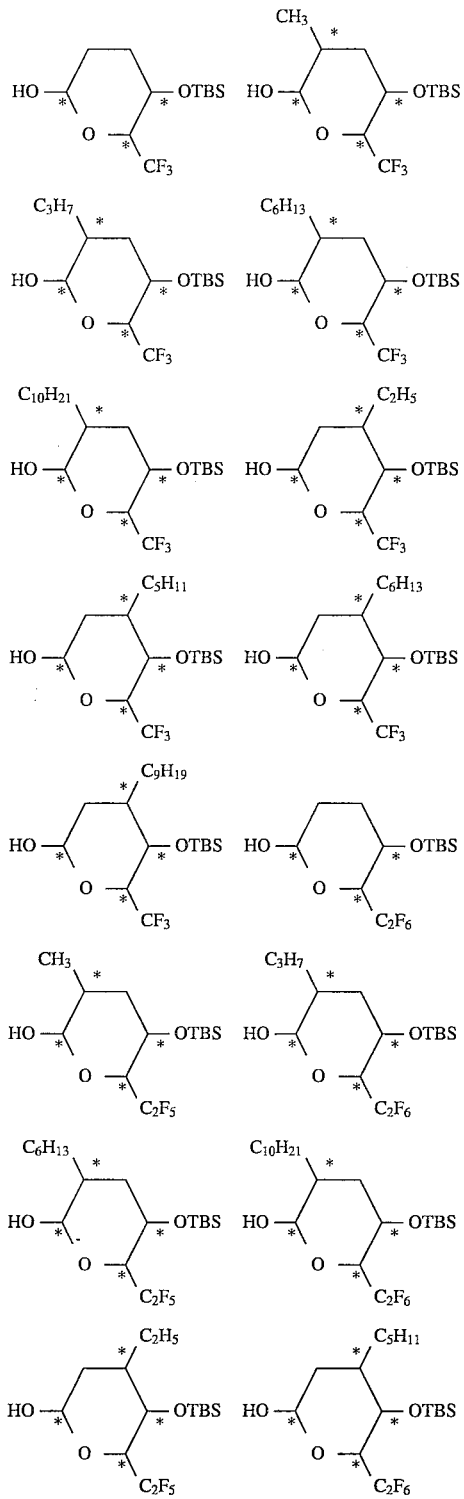

-continued
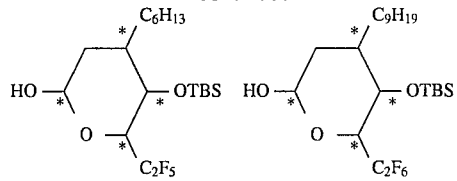
Examples of the compound represented by general formula (I) of the present invention obtained as described above include:
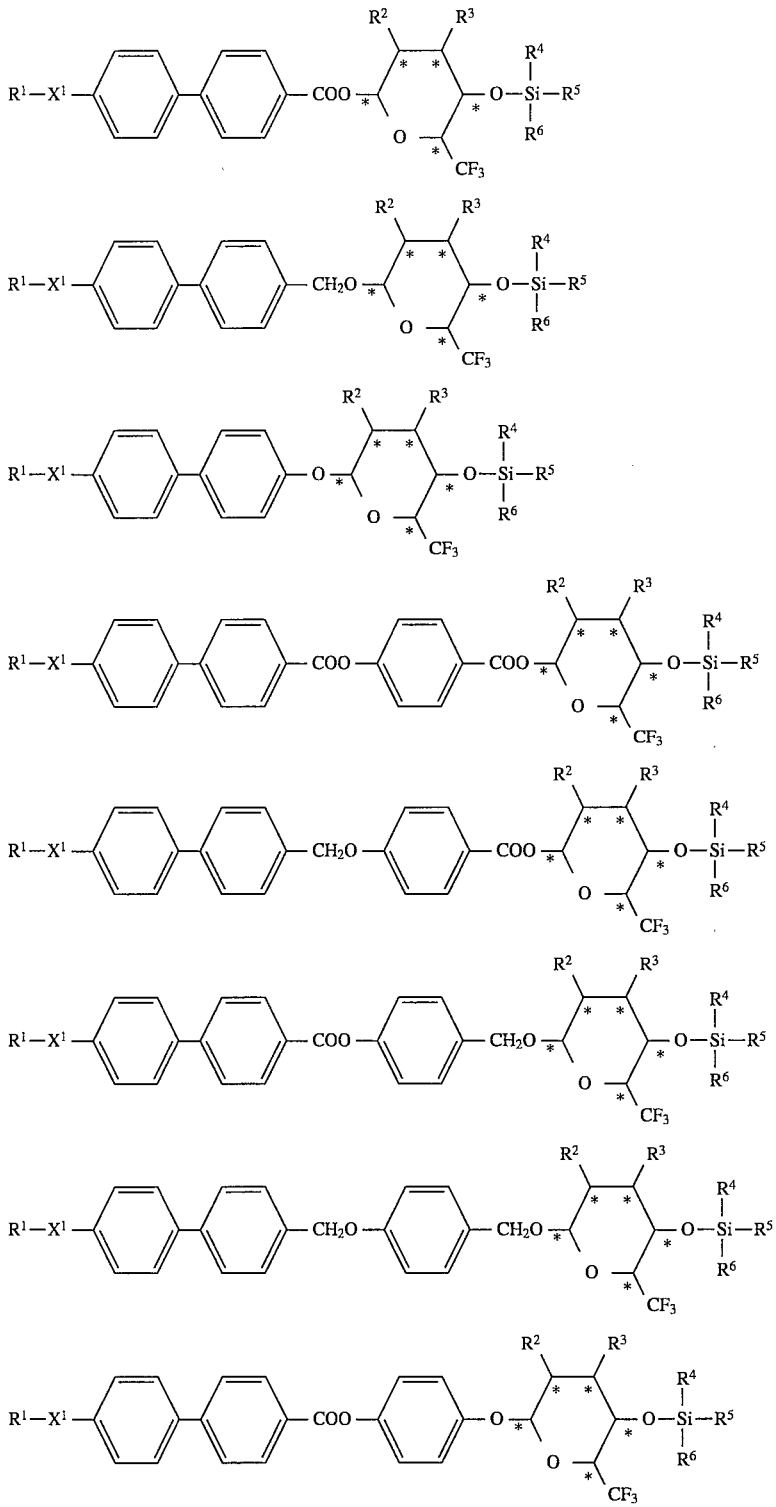

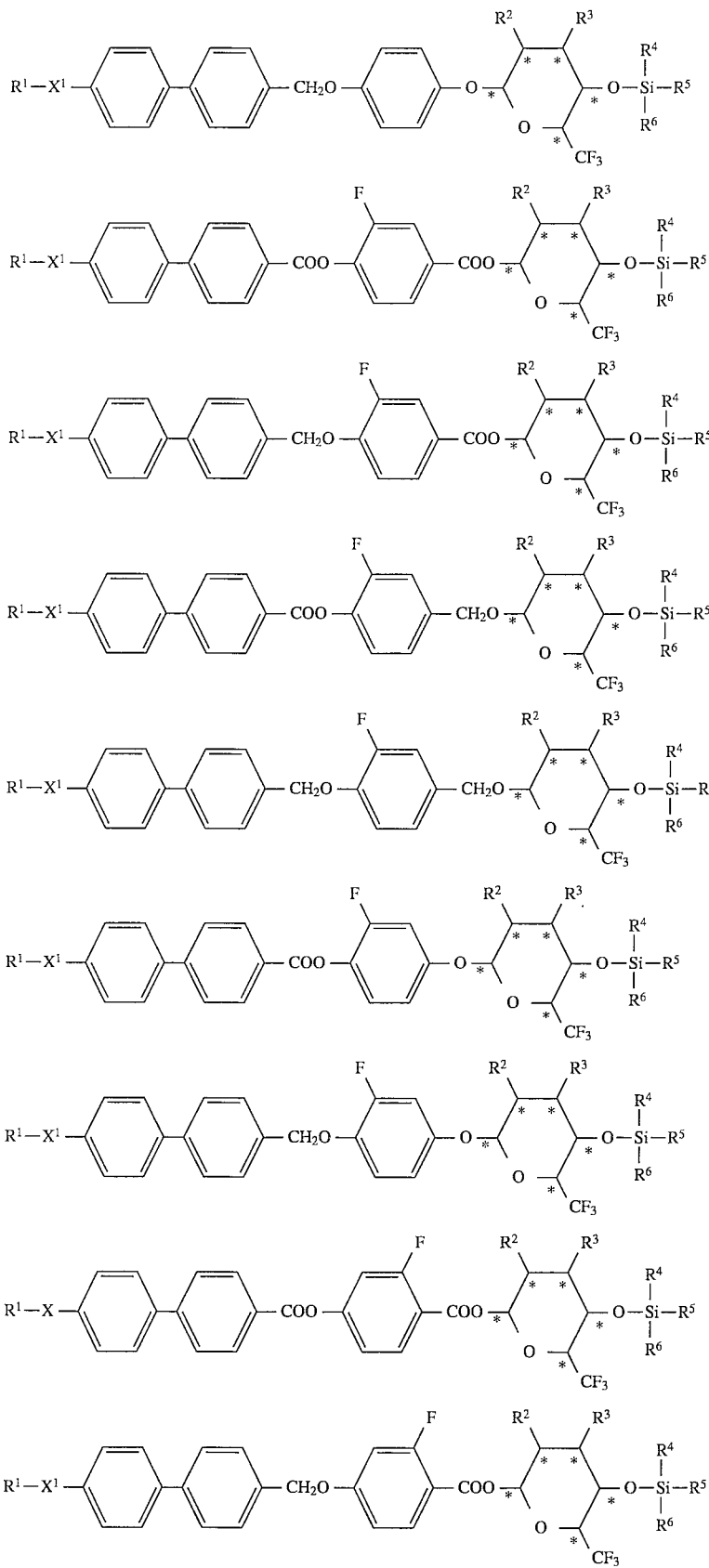

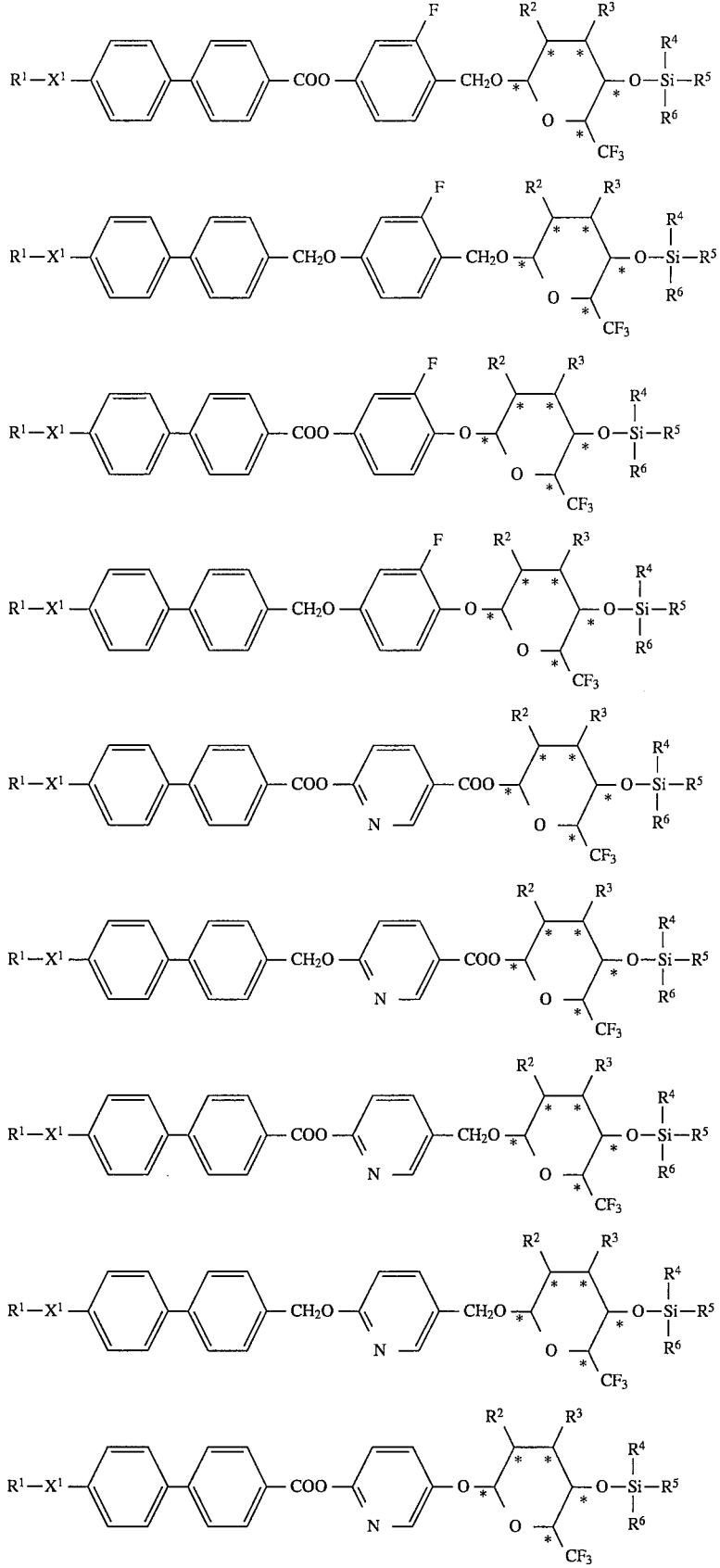

-continued
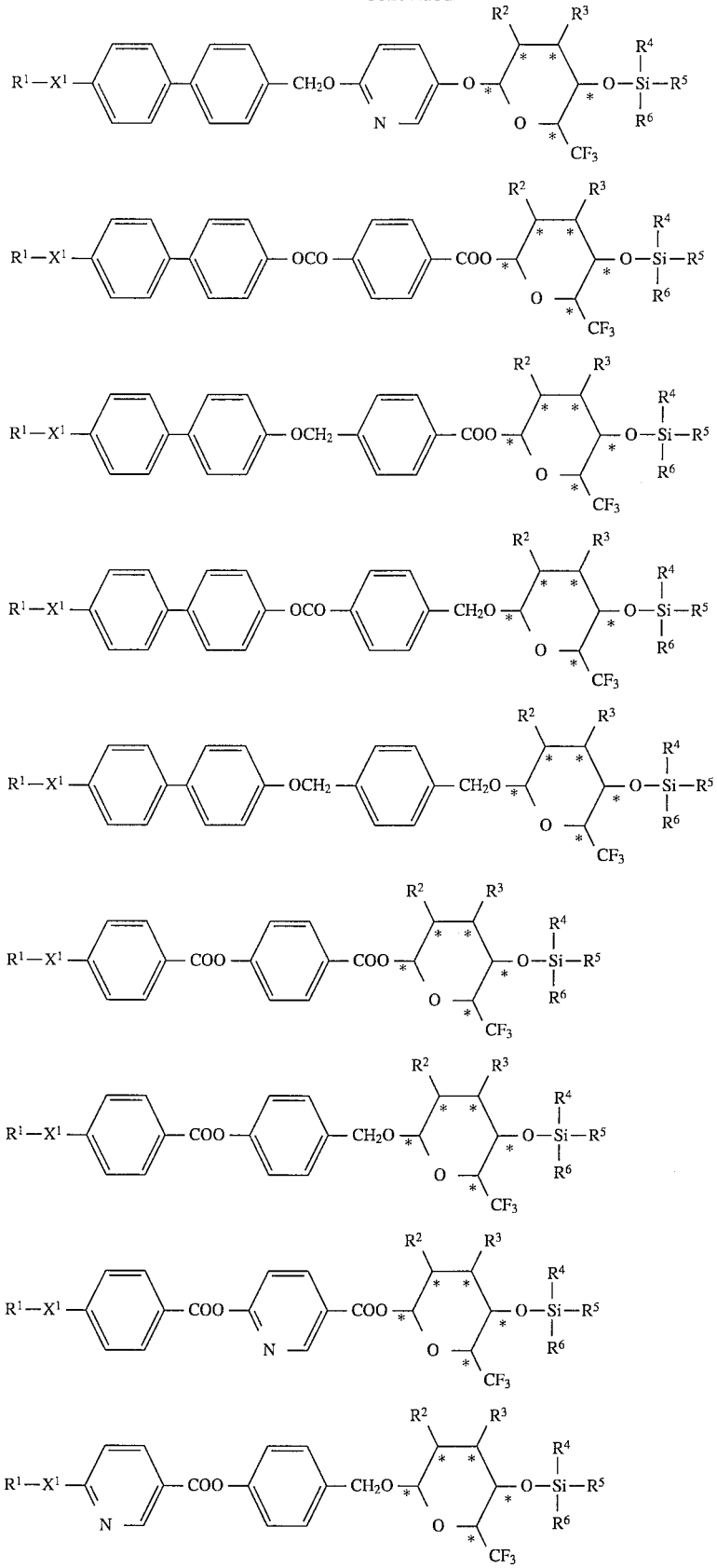

-continued
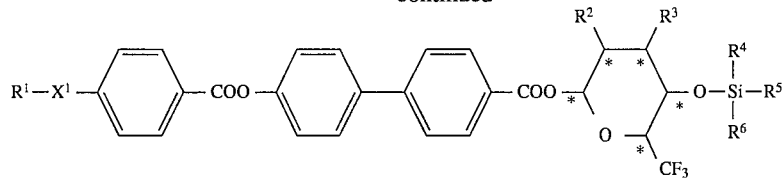
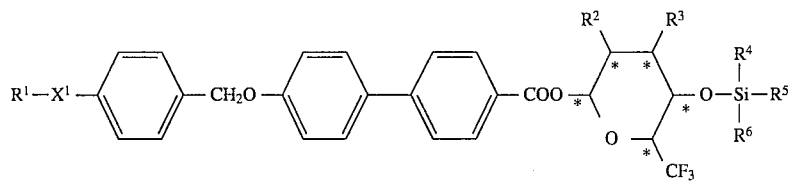
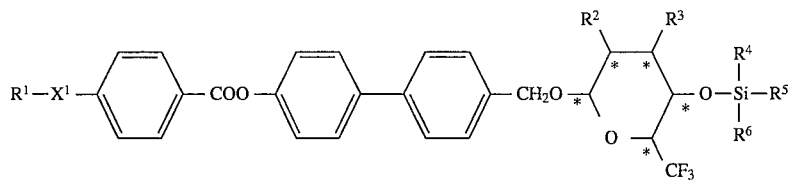
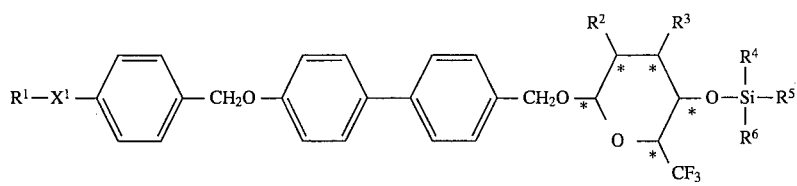
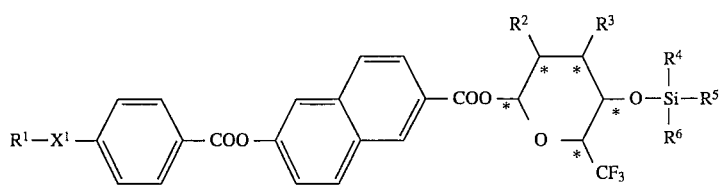
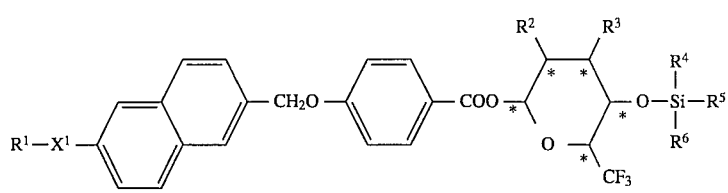
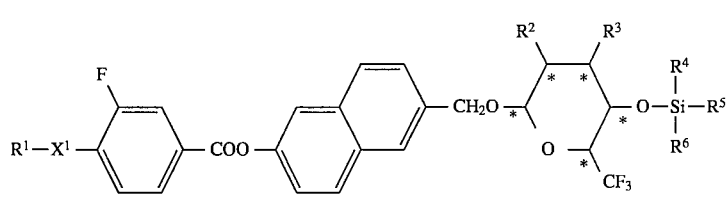
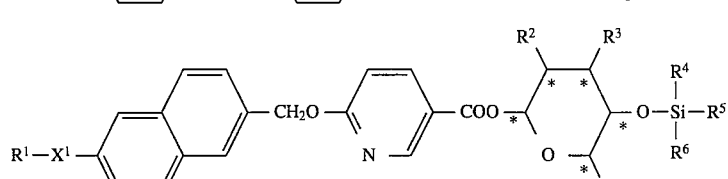
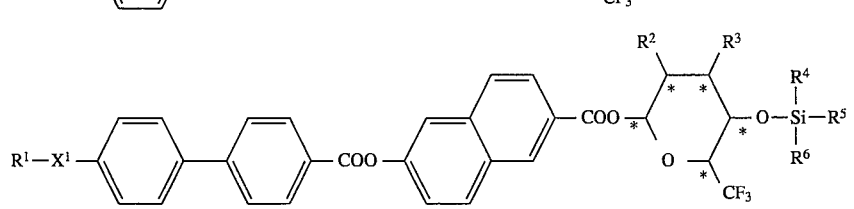

-continued
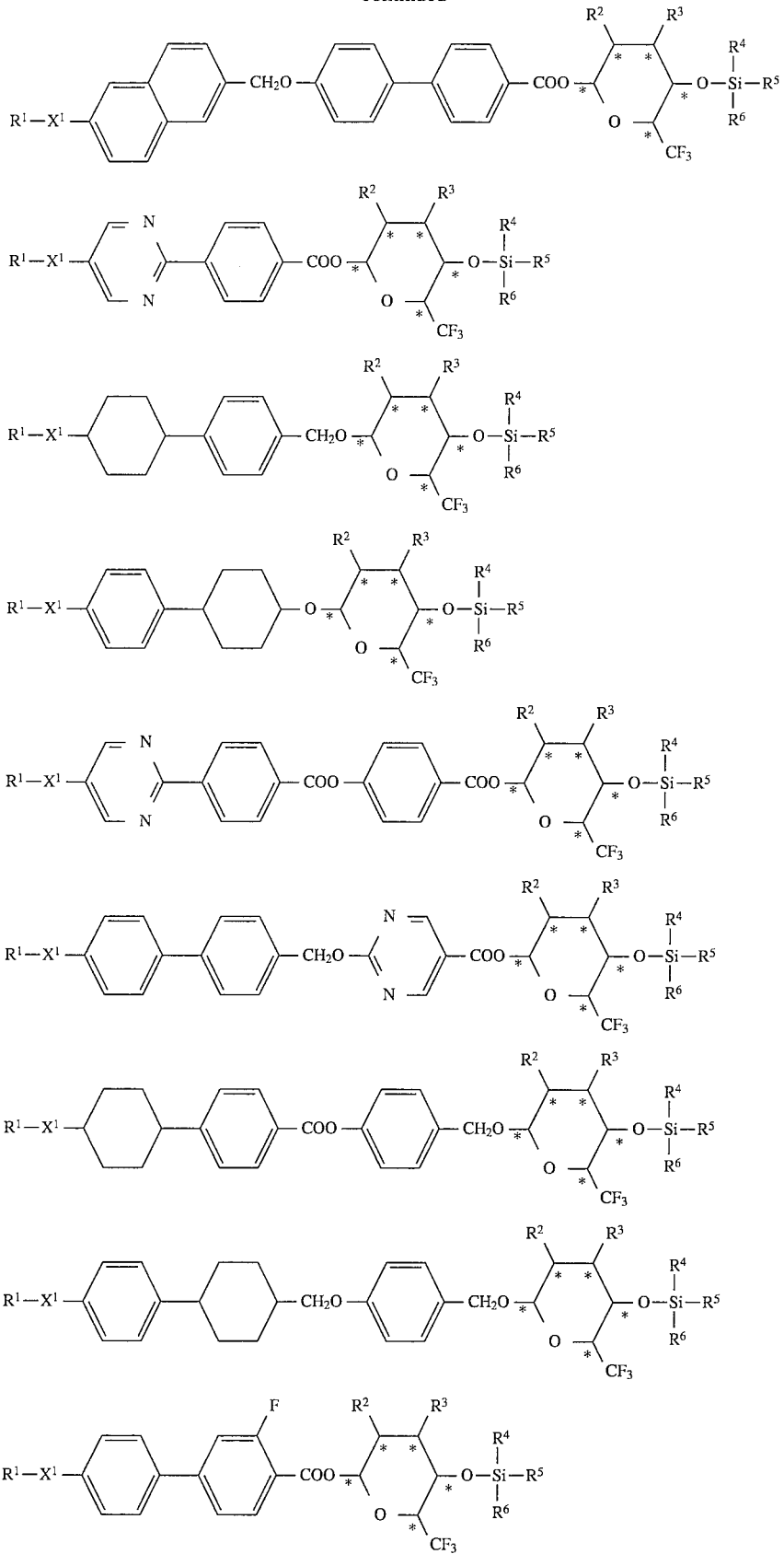

-continued
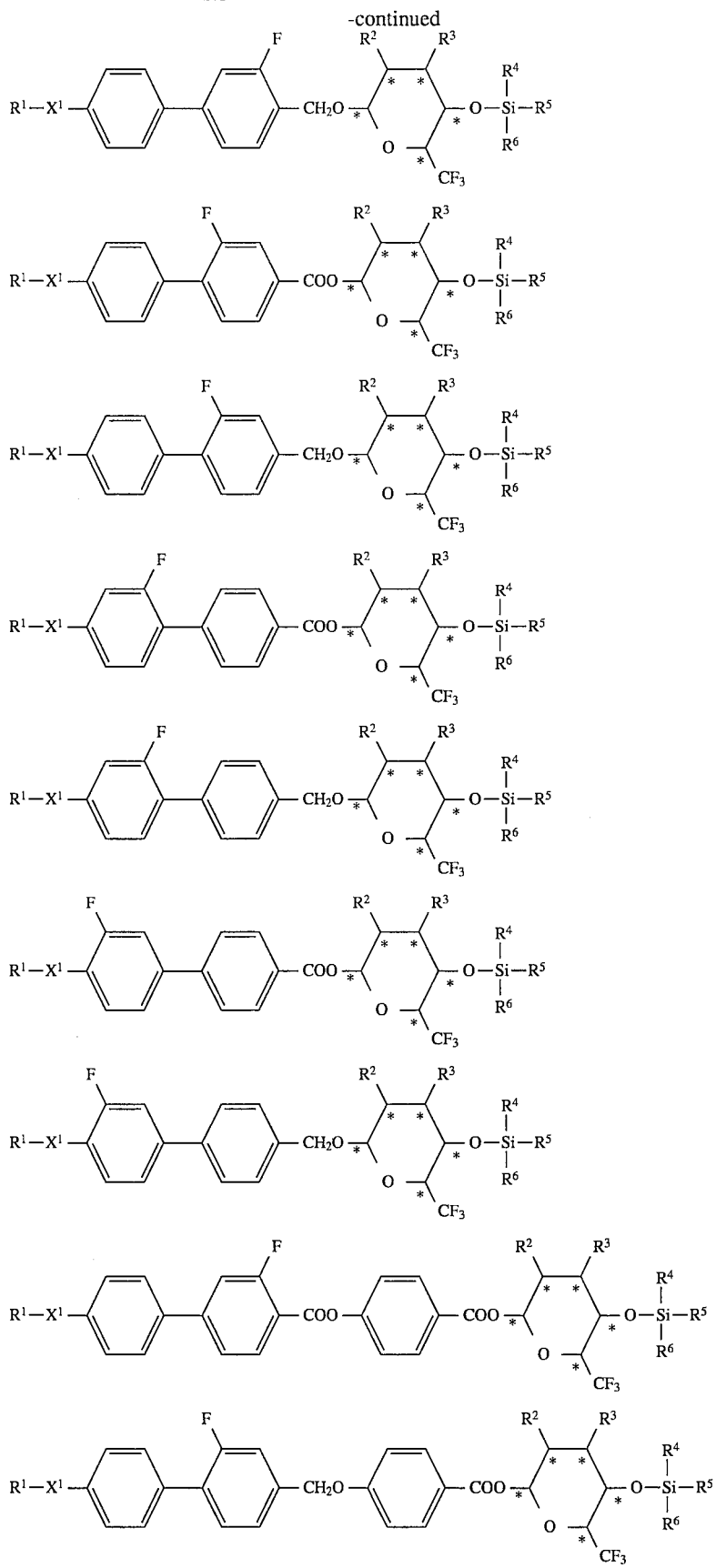

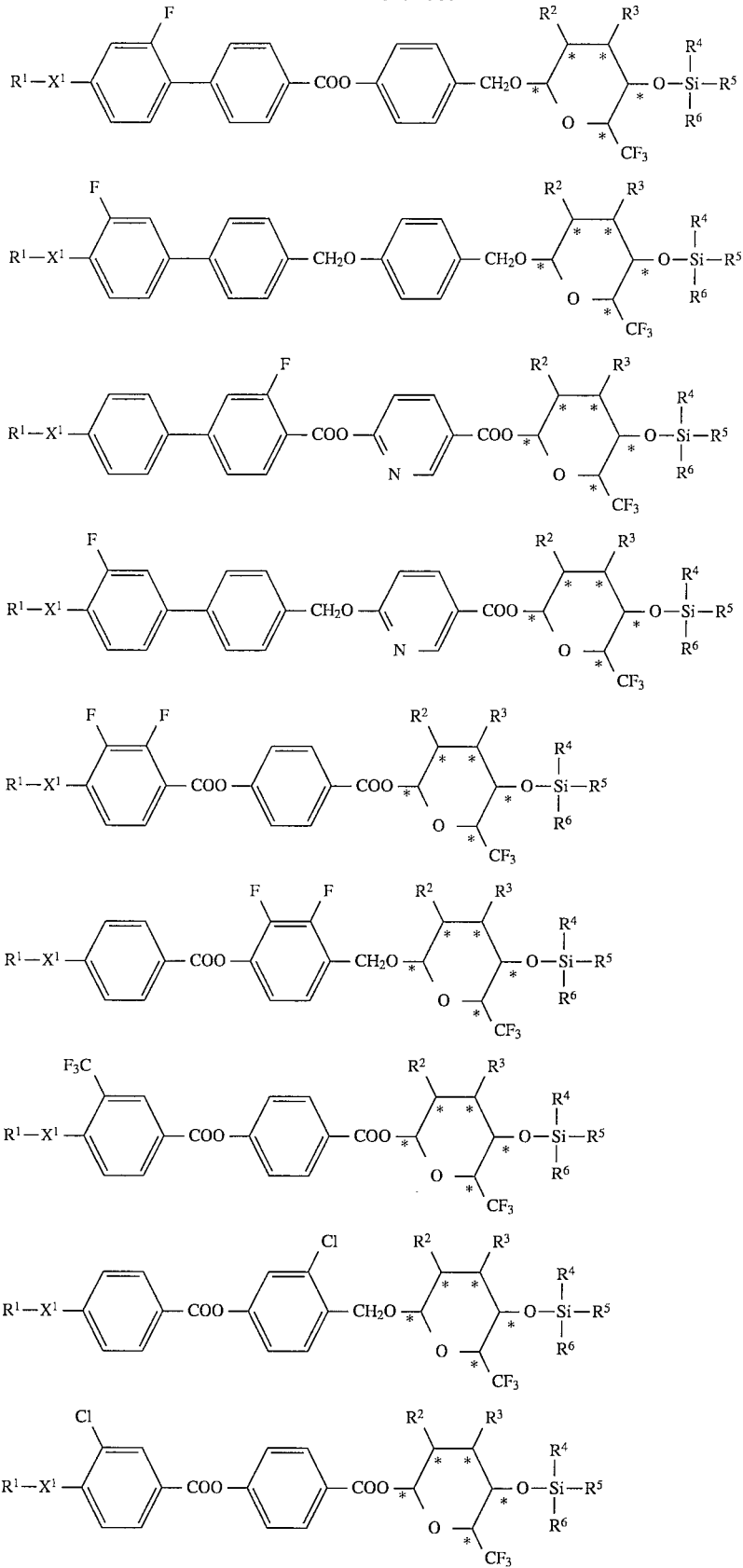

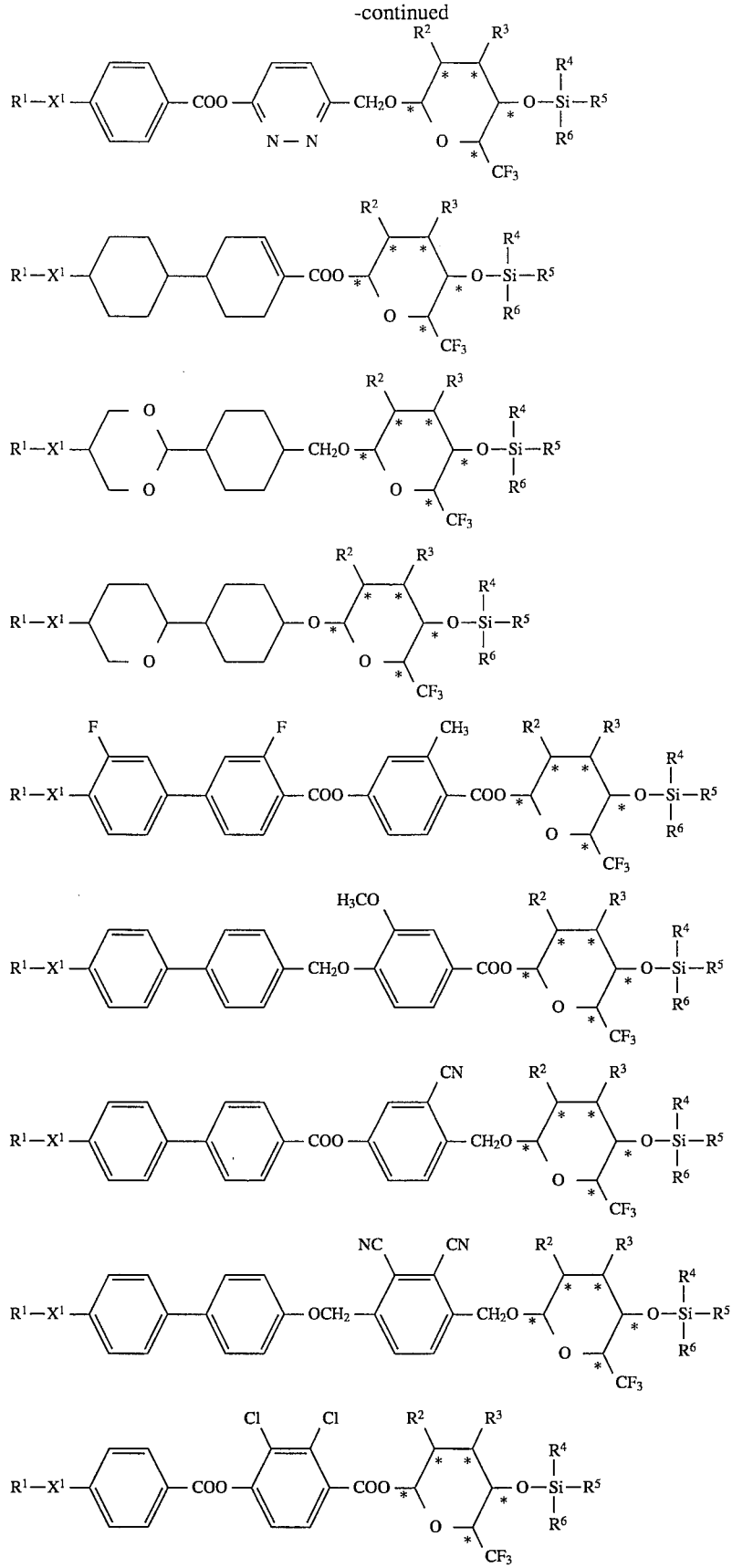

-continued
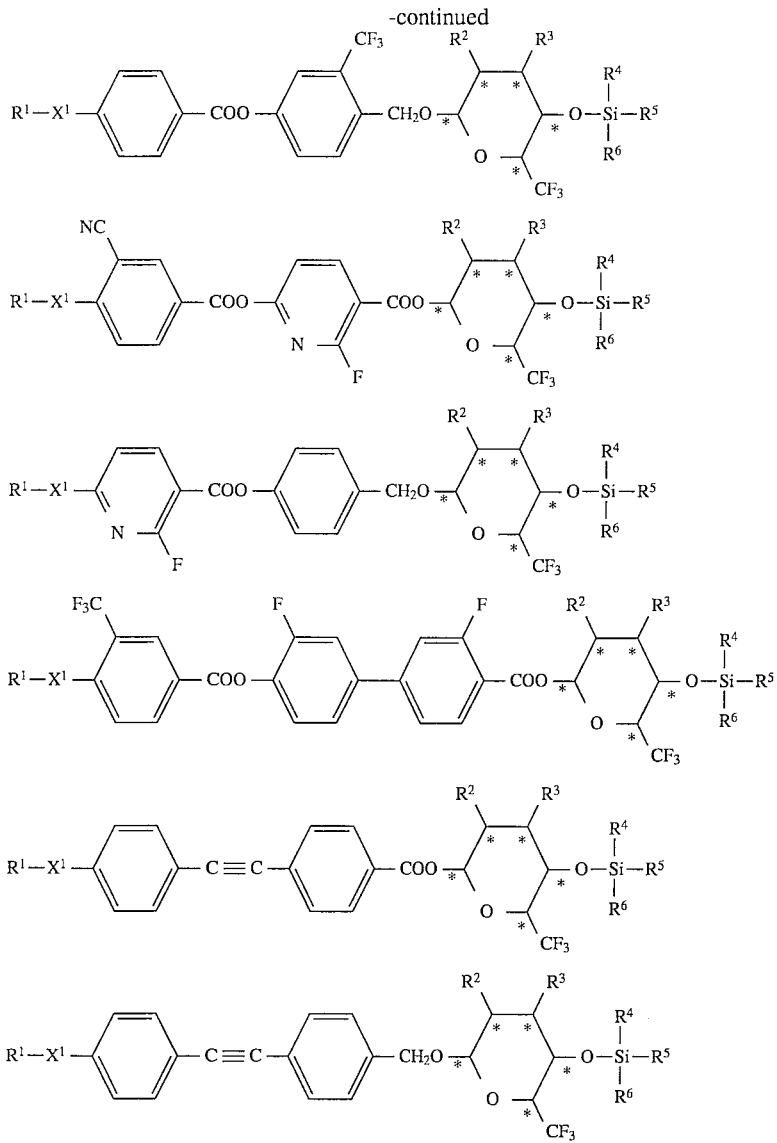
[wherein $R^1$, $X^1$, $R^2$, $R^3$, $R^4$, $R^5$, $R^6$, Si, and * are the same as those described above].
Examples of the compound represented by general formula (I') of the present invention obtained as described above include:
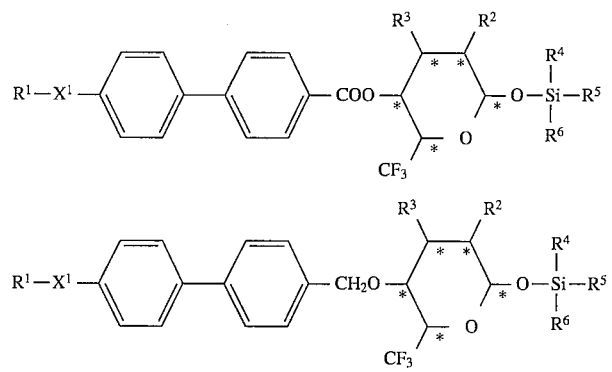

-continued
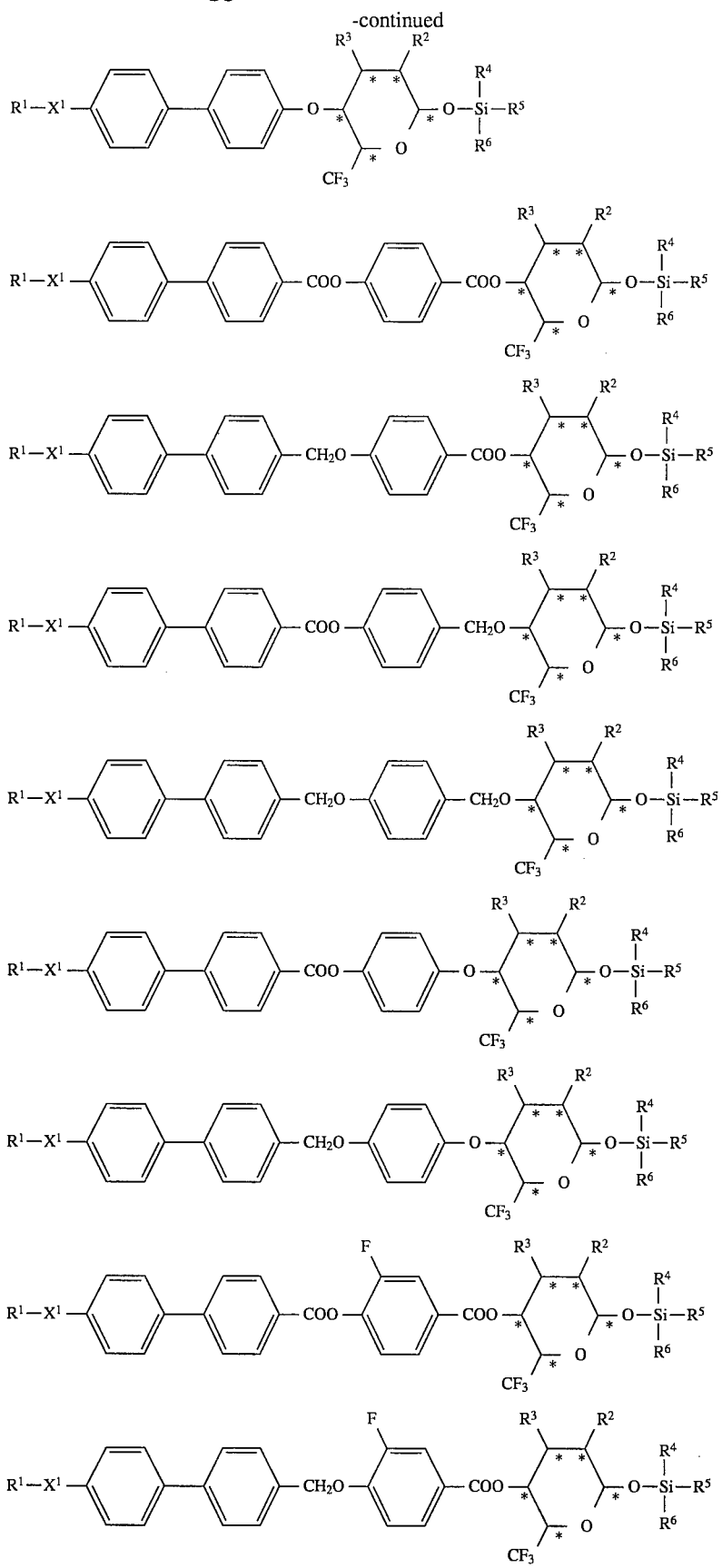

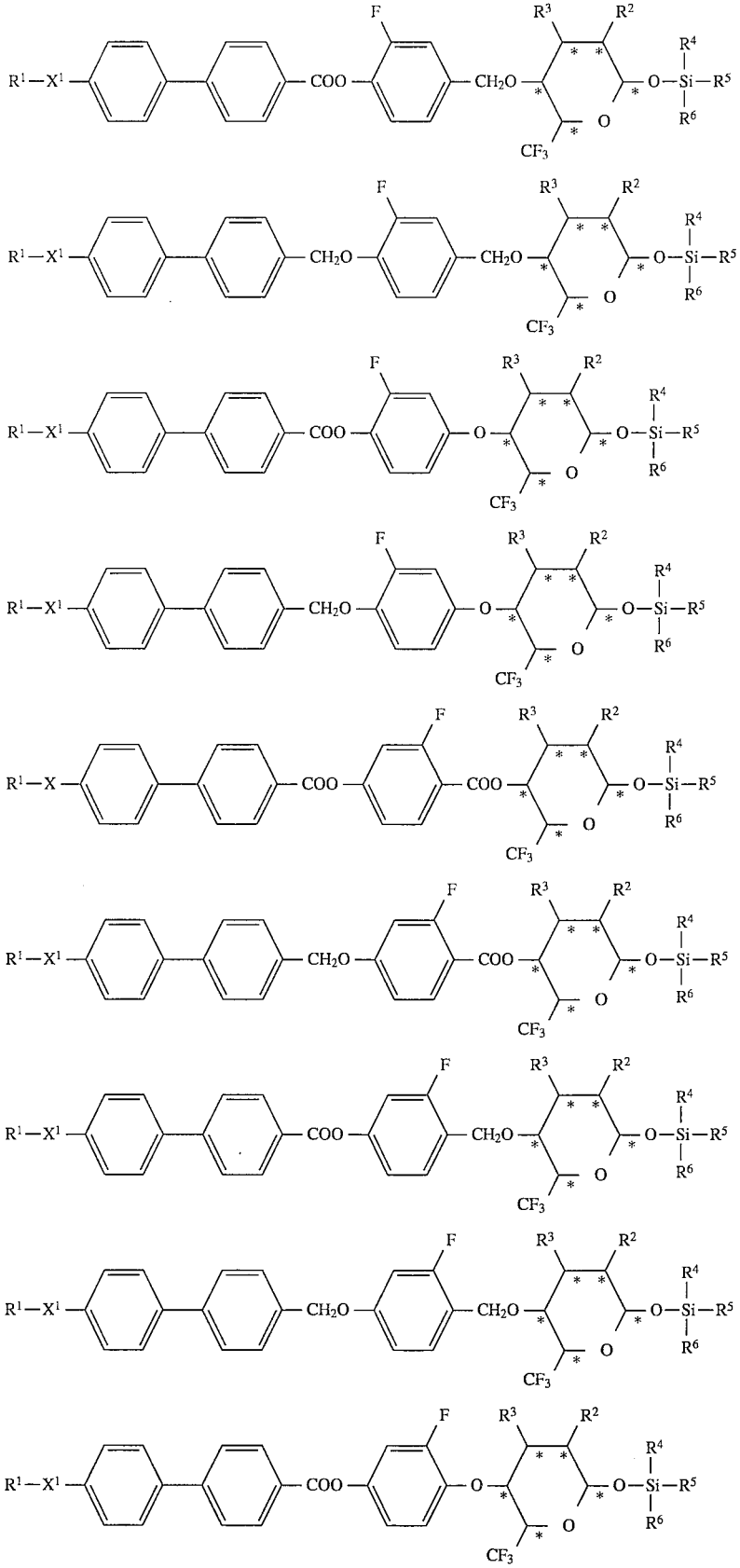

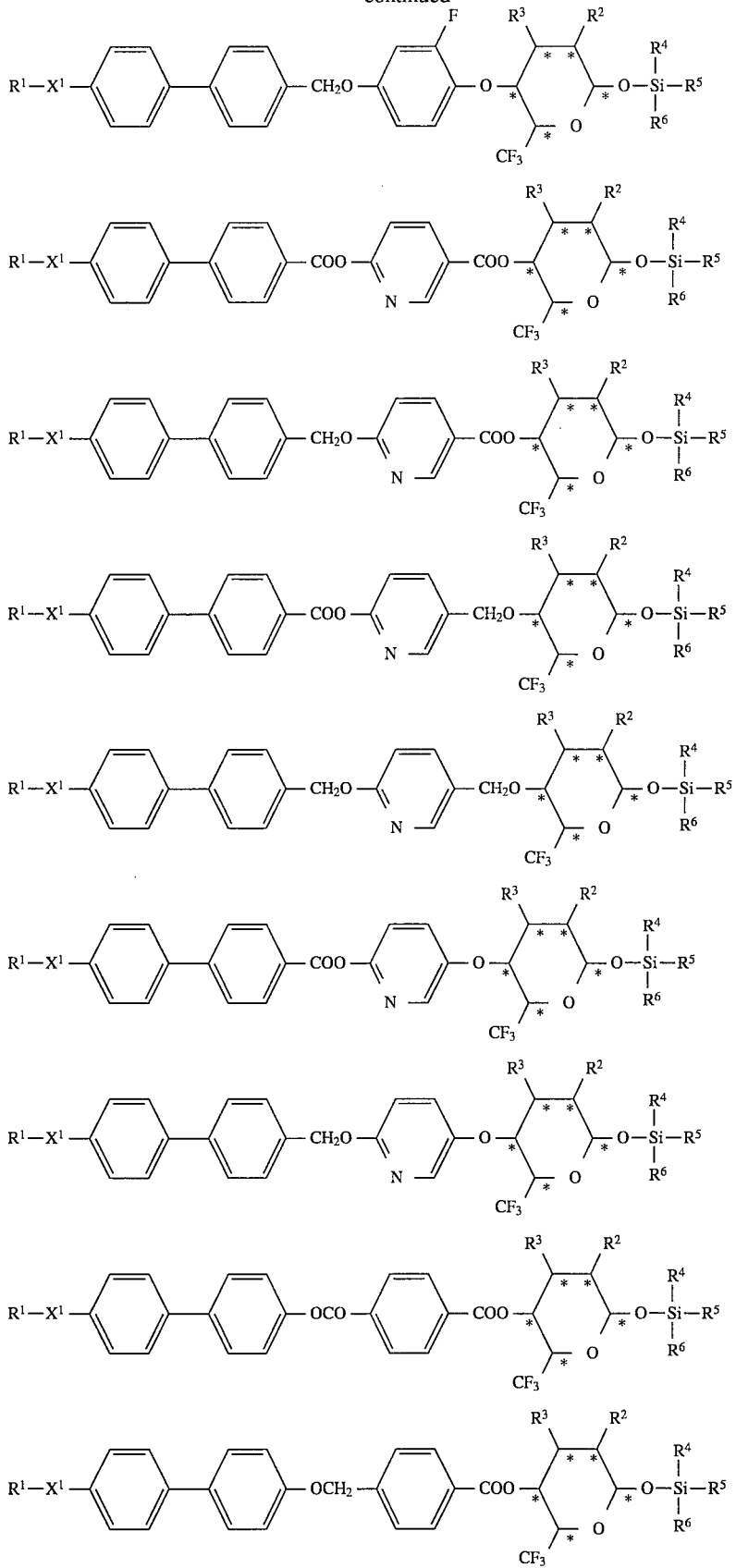

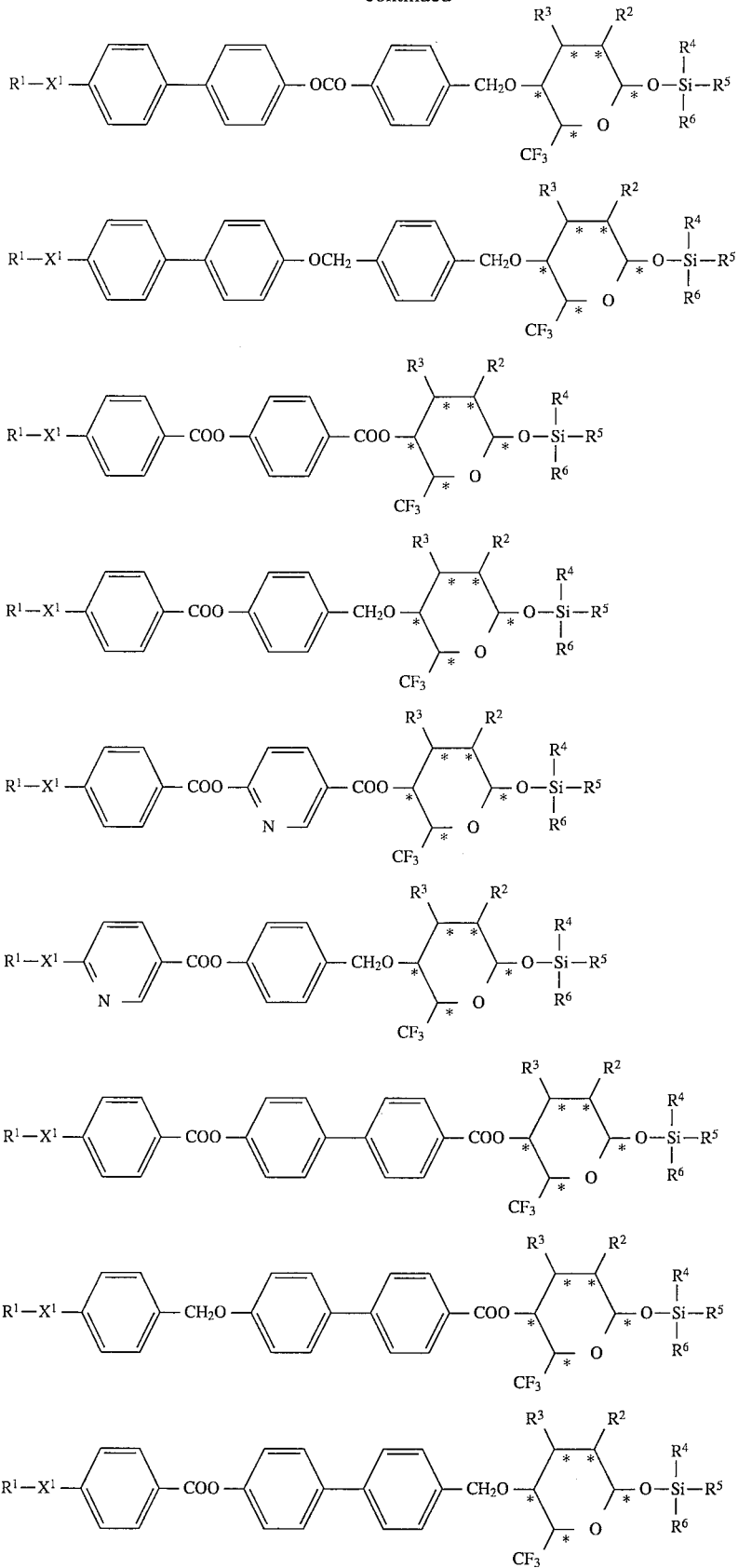

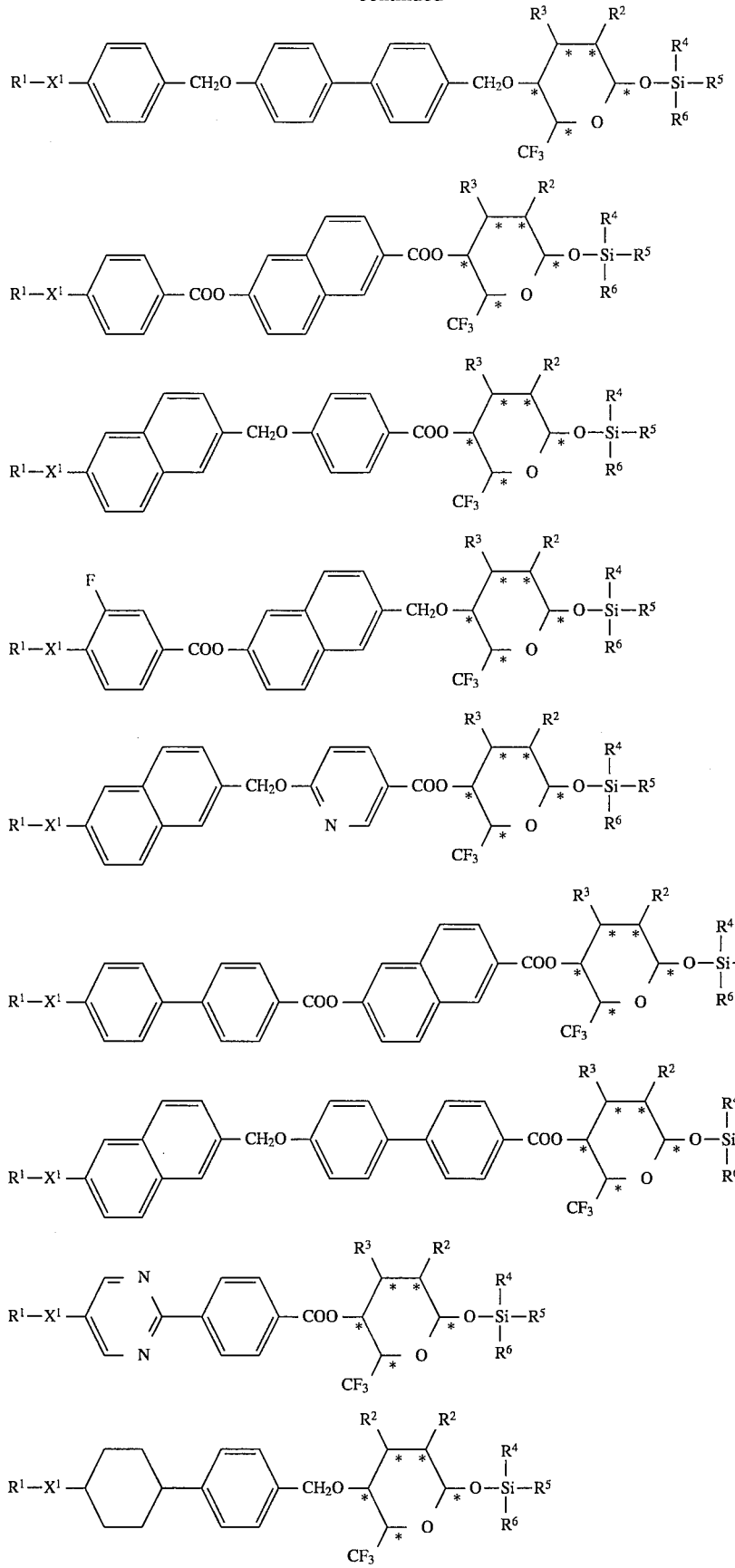

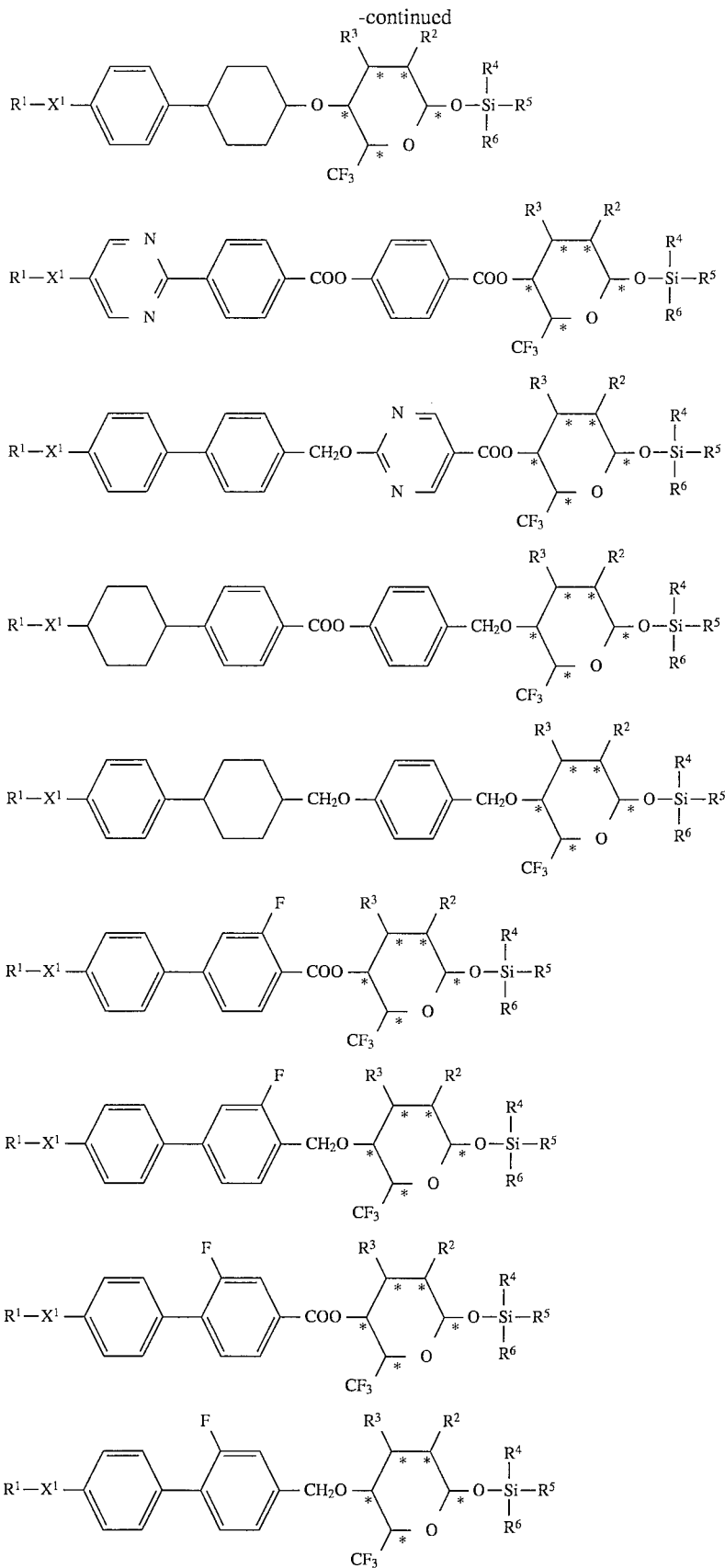

-continued
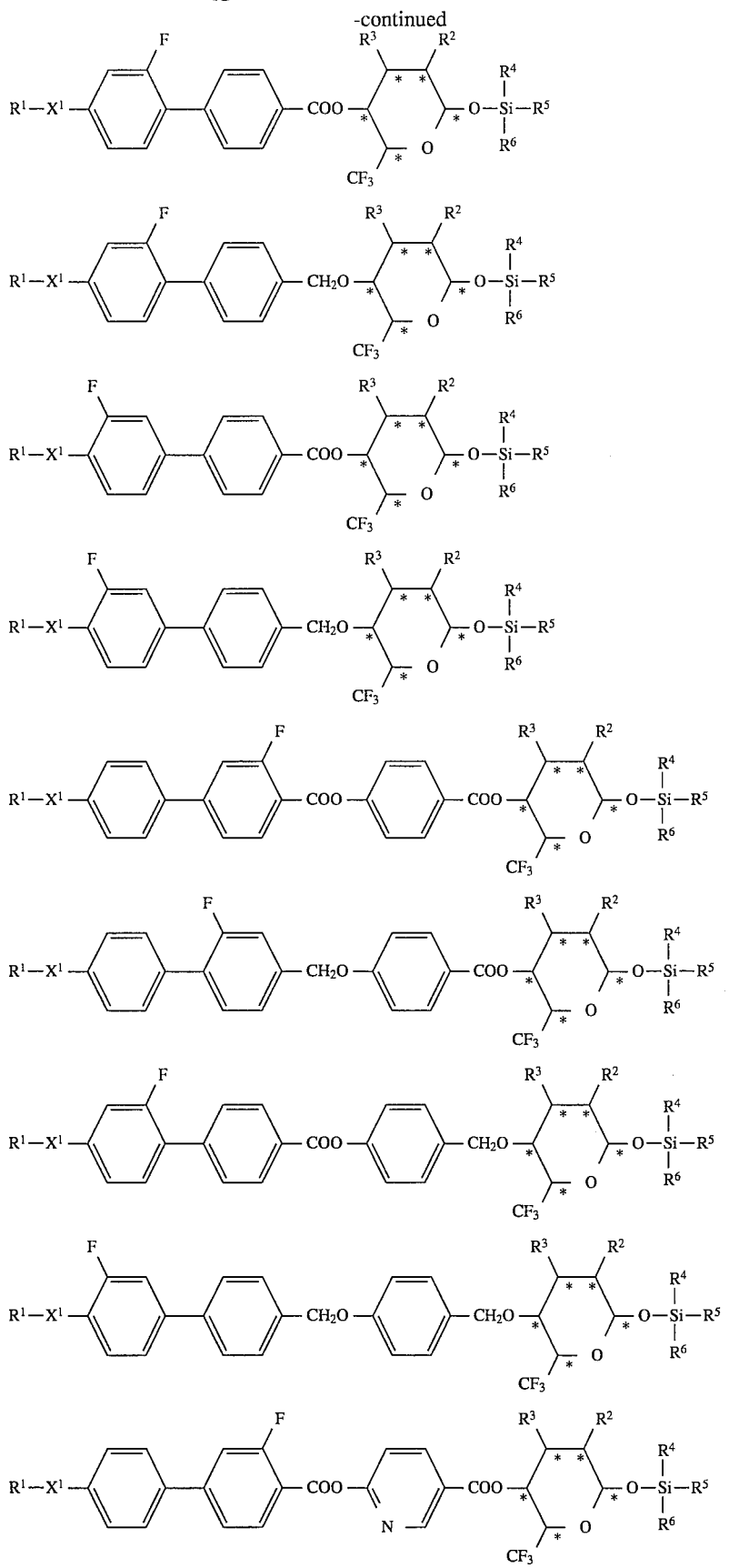

-continued
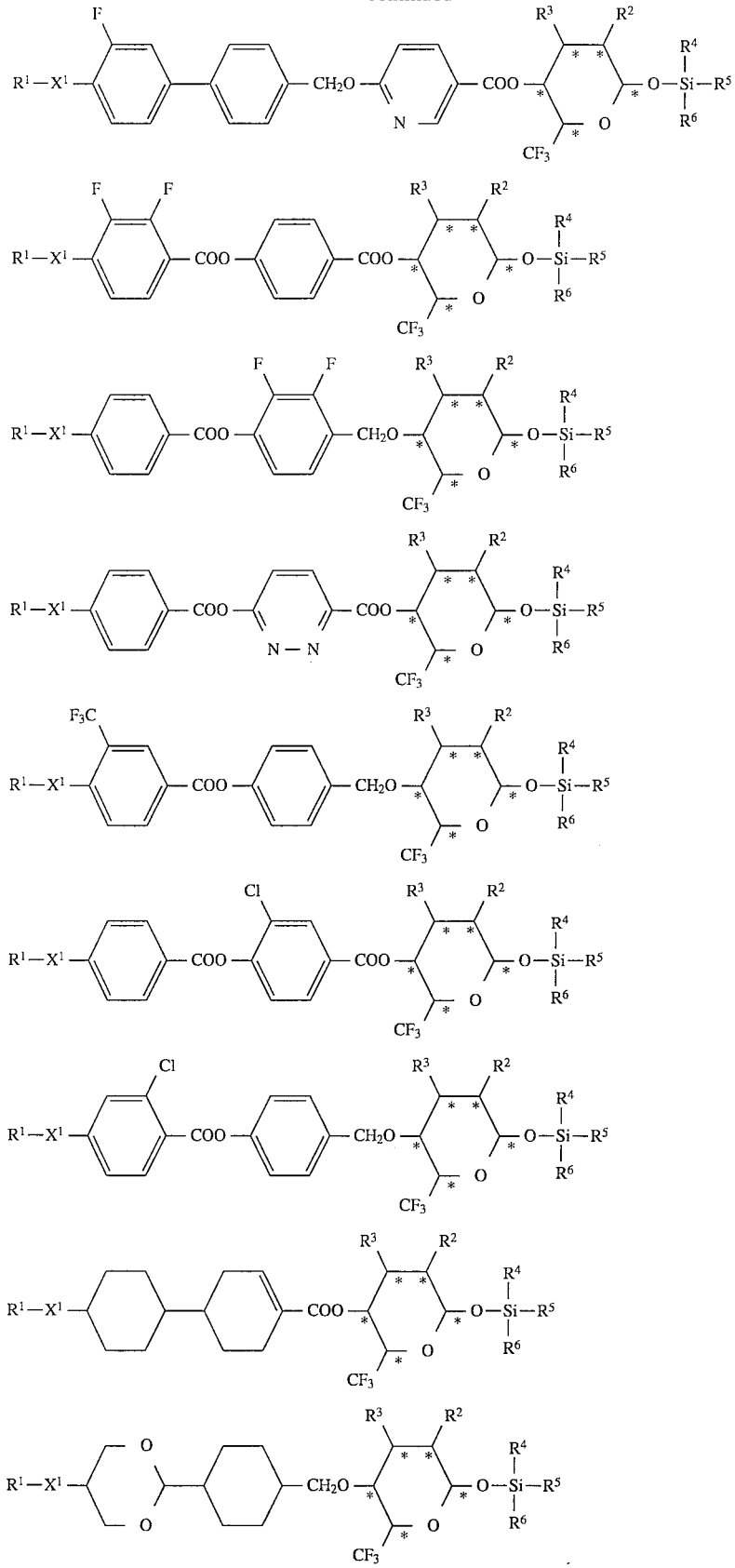

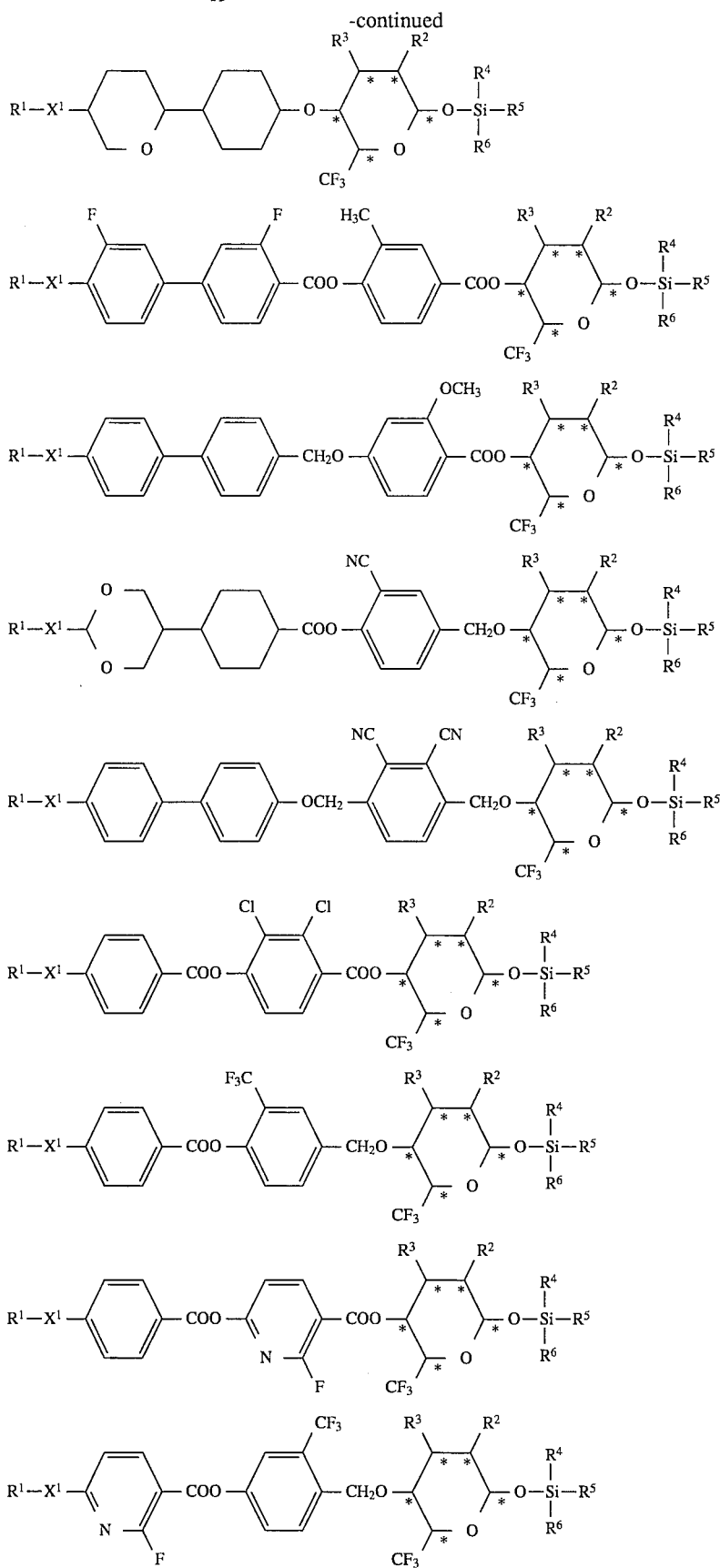

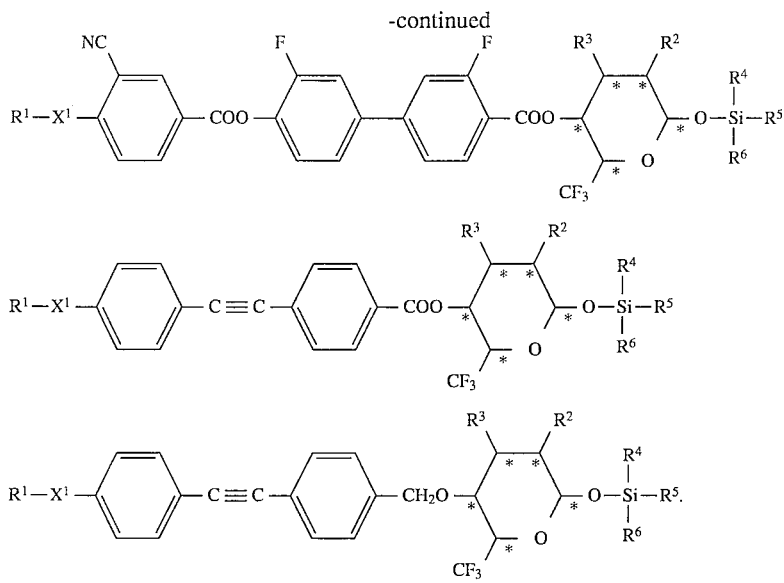

[wherein $R^1$, $X^1$, $R^2$, $R^3$, $R^4$, $R^5$, $R^6$, Si, and * are the same as those described above].

The liquid crystal composition of the present invention can be obtained by mixing (a) at least one compound selected from the compounds represented by general formula (I) or (I'); and (b) a compound or a mixture of compounds having a chiral smectic C phase (SmC*) which is different from the compound selected in (a); and/or (c) a compound or a mixture of compounds having a smectic C phase (SmC) which is different from the compound selected in (a). For mixing these components, the amount of the compound represented by general formula (I) or (I') can be suitably selected according to the situation. The amount is preferably 0.1 to 99% by weight, more preferably 1 to 90% by weight, of the liquid crystal composition obtained.

In another mode of the liquid crystal composition of the present invention, the liquid crystal composition comprises at least two types of the compound represented by general formula (I) or (I').

As compounds or mixtures of components (b) and (c) described above, various known substances can be used.

Specific examples of the compound of component (b) described above include compounds described in "Structures and Properties of Ferroelectric Liquid Crystals, by Fukuda and Takezoe, published by Corona Co. in 1990, Page 229, Table 7.1". More specific examples include the following compounds:

compounds containing 

such as:

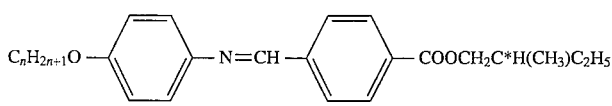

compounds containing 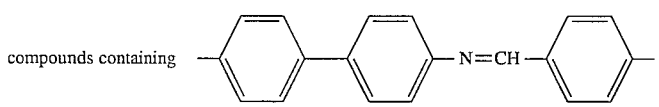

such as:

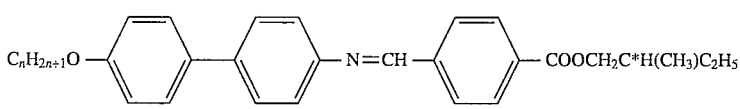

compounds containing 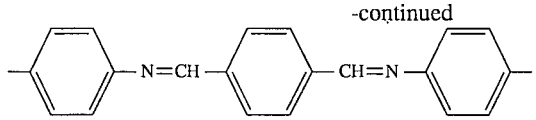

such as:

C$_2$H$_5$C*H(CH$_3$)CH$_2$OCOCCl=CH 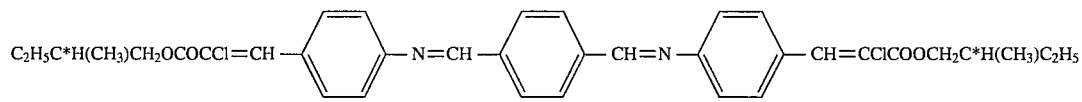 CH=CClCOOCH$_2$C*H(CH$_3$)C$_2$H$_5$ compounds containing 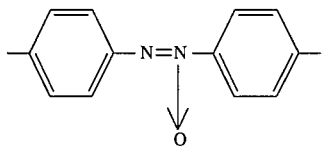

such as:

C$_2$H$_5$C*H(CH$_3$)C$_n$H$_{2n}$O 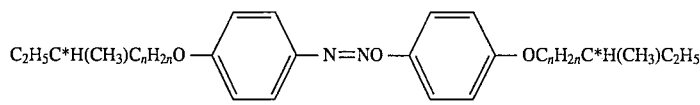 OC$_n$H$_{2n}$C*H(CH$_3$)C$_2$H$_5$ compounds containing 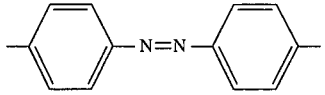

such as:

C$_{16}$H$_{33}$O 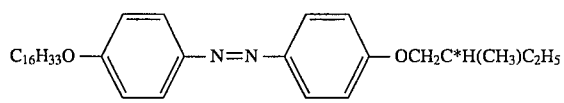 OCH$_2$C*H(CH$_3$)C$_2$H$_5$ compounds containing 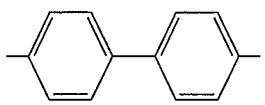

such as:

C$_8$H$_{17}$O 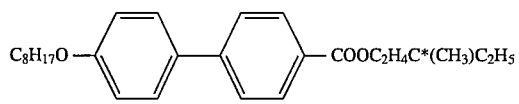 COOC$_2$H$_4$C*(CH$_3$)C$_2$H$_5$ compounds containing 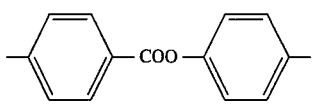

such as:

C$_n$H$_{2n+1}$O 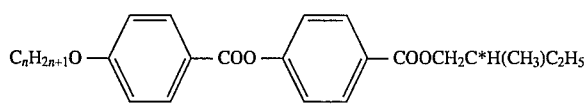 COOCH$_2$C*H(CH$_3$)C$_2$H$_5$

C$_n$H$_{2n+1}$O 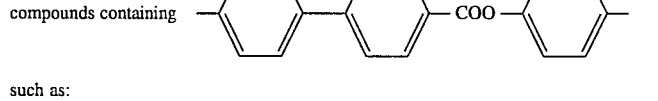 OC$_5$H$_{10}$C*H(CH$_3$)C$_2$H$_5$ compounds containing 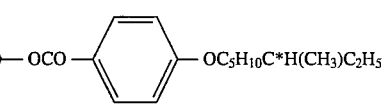

such as:

C$_n$H$_{2n+1}$ 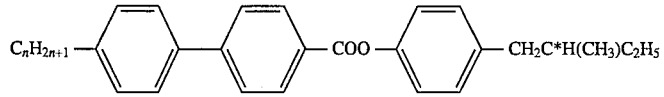 CH$_2$C*H(CH$_3$)C$_2$H$_5$

compounds containing 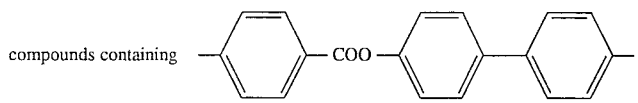
such as:
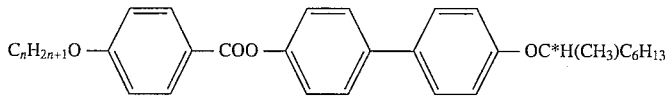
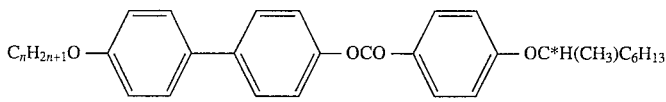
compounds containing 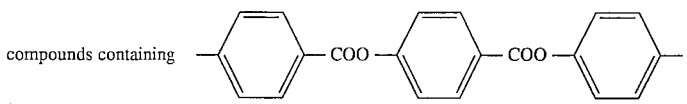
such as:
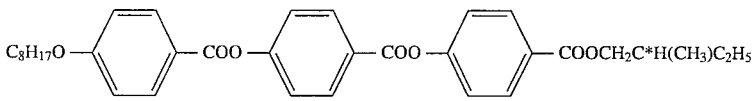
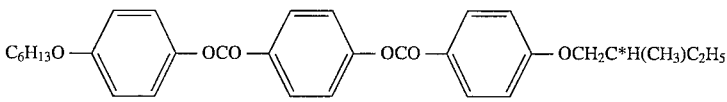
compounds containing 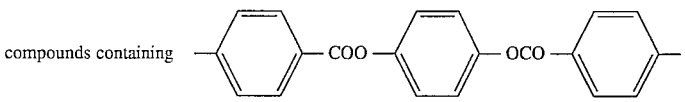
such as:
compounds containing 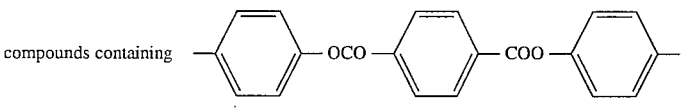
such as:
compounds containing 
such as:
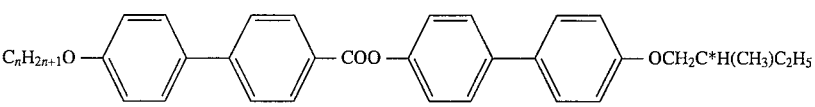

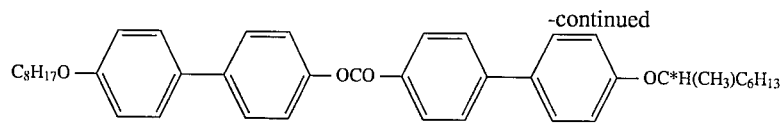
compounds containing 
such as:
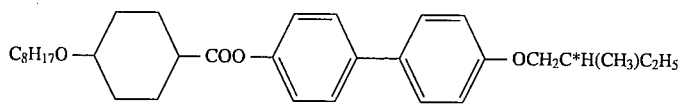
compounds containing 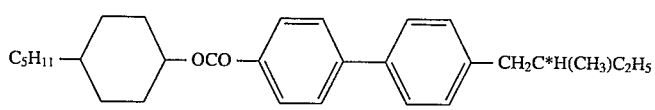
such as:
compounds containing 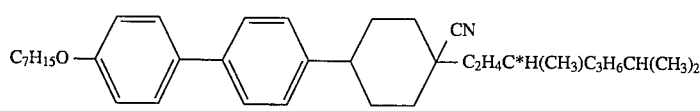
such as:
compounds containing 
compounds containing 
compounds containing 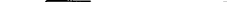
compounds containing 
compounds containing 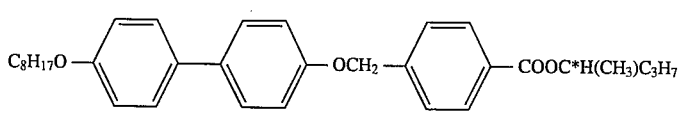
such as:

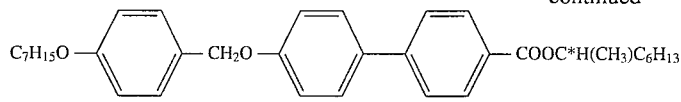
compounds containing 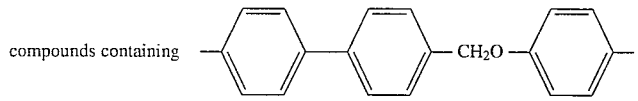
such as:
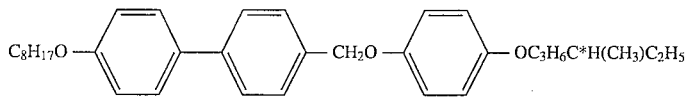
compounds containing 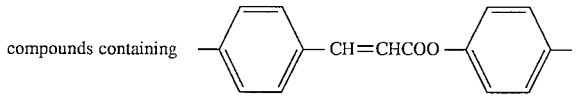
such as:
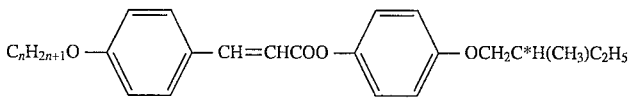
compounds containing 
such as:
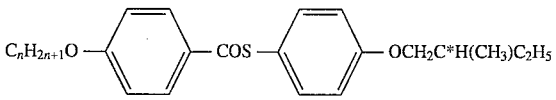
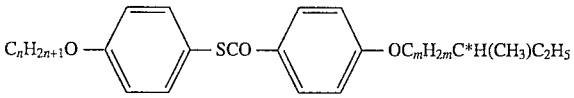
compounds containing 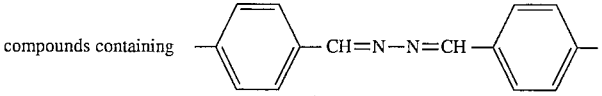
such as:
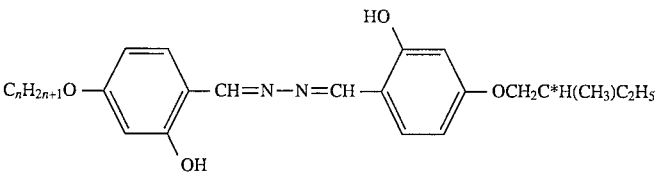
compounds containing 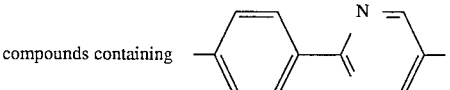
such as -continued
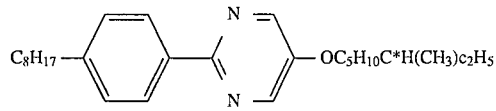
compounds containing 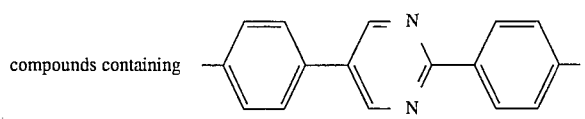
such as:
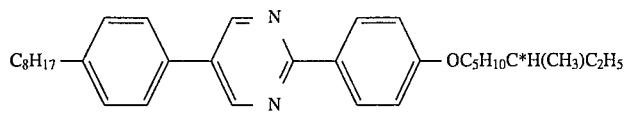
compounds containing 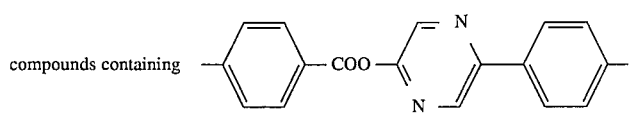
such as:
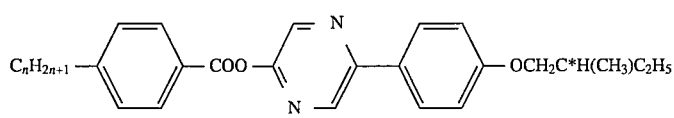
compound containing 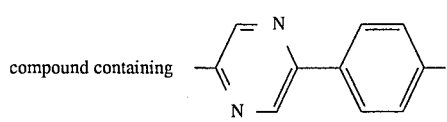
such as:
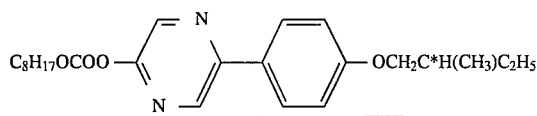
compound containing 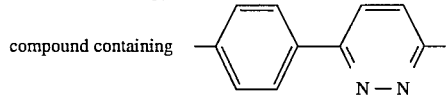
such as:
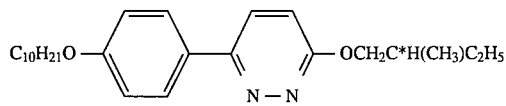
compound containing 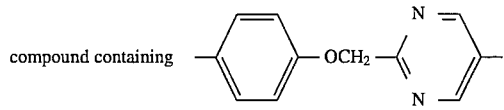
such as:
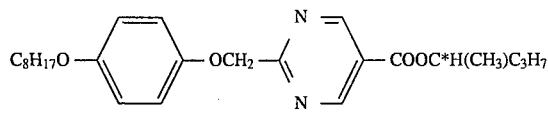

compounds containing 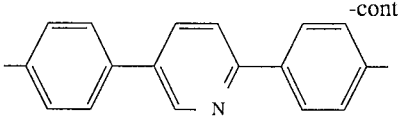
such as:
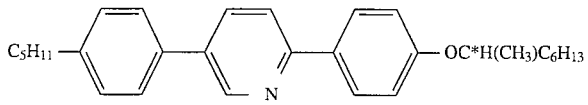
compounds containing 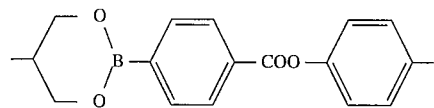
such as:
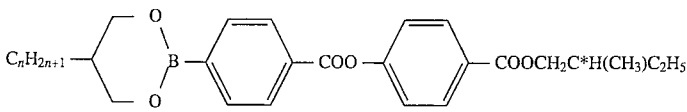
compounds containing 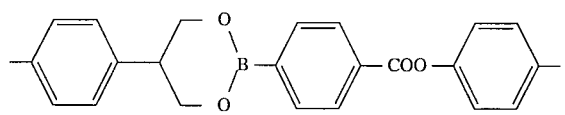
such as:
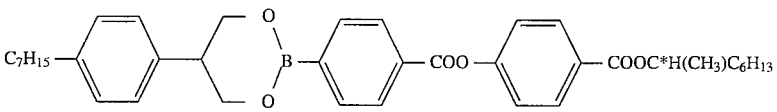
compounds containing 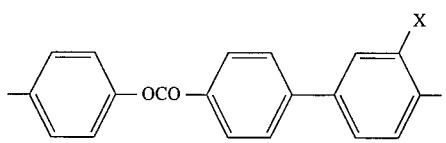
such as:
X:H,F,Cl,Br,CN
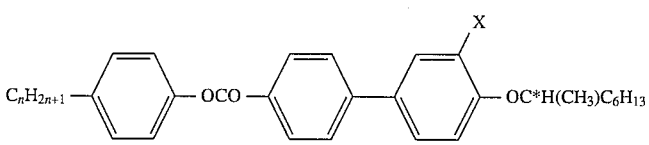
compounds containing 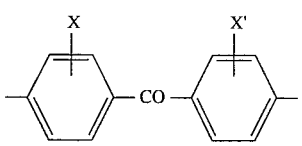
such as:
X:H,H,H,H,3-F,3-Cl,2-F,2-Cl
X':3'F,3'-Cl,2'-F,2'-Cl,H,H,H,H
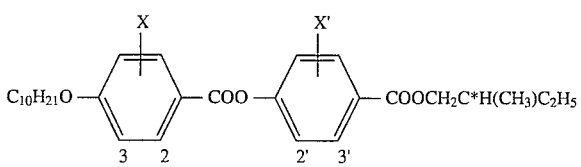

compounds containing 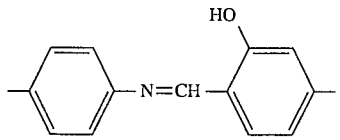

such as:

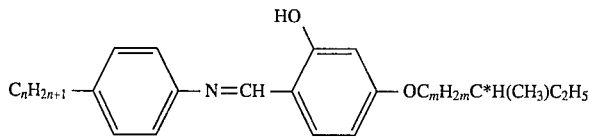

Preferable examples of the compound of component (c) include compounds represented by the following general formula (A):

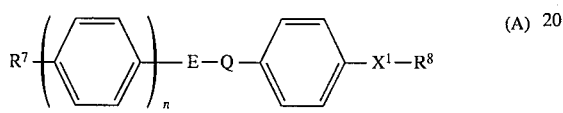

[wherein $R^7$ represents an alkyl or alkoxy group having 1 to 15 carbon atoms which may have a substituent, $R^8$ represents an alkyl group having 1 to 15 carbon atoms which may have a substituent, Q represents —O—, —COO—, —OCO—, —OCOO—, or a single bond, E represents

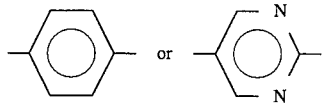

n represents 0 or 1, and $X^1$ is the same as that described above]. Specific examples of the compound of component (c) include the following compounds:

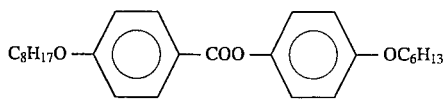

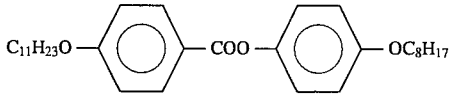

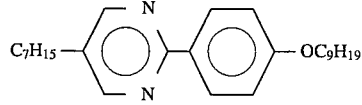

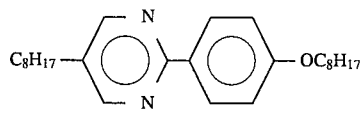

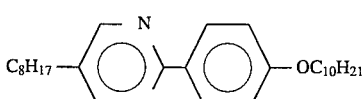

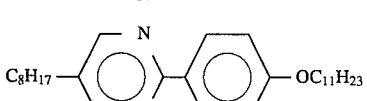

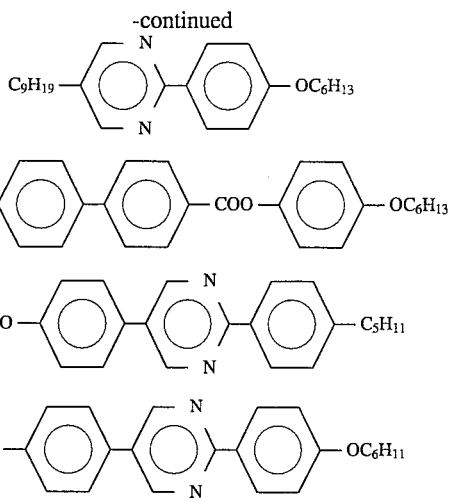

The liquid crystal device of the present invention comprises a pair of electrode plates and the compound represented by general formula (I) or (I') described above or the liquid crystal composition described above which is placed between the pair of electrode plates. The electrode plate comprises a transparent plate, a transparent electrode which is made from, for example, $InO_3$, $SnO_2$, or ITO (a mixed oxide of indium oxide and tin oxide) and placed on the transparent plate, and an alignment film which is made from polyvinyl alcohol or polyimide and placed on the other face of the transparent electrode. The liquid crystal device of the present invention may also comprise the pair of electrode plates described above, the compound described above or the liquid crystal composition described above which is placed between the pair of electrode plates, and polarizing plates which are placed on the outer faces of both electrode plates. This device can be used as a display device or an electrooptical device by making use of the birefringence mode.

To summarize the advantages obtained by the invention, the optically active tetrahydropyran derivative of the present invention is a novel compound which is chemically stable, causes no coloring, has excellent optical stability, and shows a large spontaneous polarization and a high speed response.

Therefore, the optically active tetrahydropyran derivative of the present invention can show a more excellent high speed response when it is used in a composition, and is useful as a component in a ferroelectric liquid crystal which induces a large spontaneous polarization.

The invention will be understood more readily with reference to the following reference examples and examples; however, these reference examples and examples are intended to illustrate the invention and are not to be construed to limit the scope of the invention.

In the following examples, the R form or the S form of the optically active compound represented by general formula (I) or (I') is indicated by the combination of the position number shown in the following formulae and R or S, respectively:

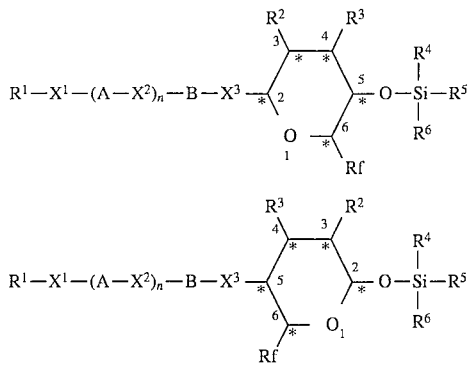

[wherein Rf, $R^1$, $R^2$, $R^3$, $R^4$, $R^5$, $R^6$, $X^1$, $X^2$, $X^3$, A, B, Si, n, and * are the same as those described above].

Reference Example 1

Synthesis of
(5S,6S)-tetrahydro-5-t-butyldimethylsiloxy-
6-trifluoromethyl-2-hydroxypyran

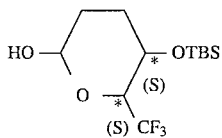

[wherein TBS and * are the same as those described above].

(a) To a solution prepared by dissolving 13.6 g (200 mmol) of furan in 150 ml of tetrahydrofuran, was added dropwise 133 ml (200 mol) of a 1.5 mol/liter hexane solution of n-butyllithium at −20° C. under nitrogen atmosphere, and the reaction was allowed to proceed for 1 hour. Then, 21.7 g (200 mmol) of trimethylsilyl chloride was added dropwise to the reaction solution, and the solution was kept stirring at −20° C. for 1 hour. After adding 133 ml (200 mmol) of a 1.5 mol/liter hexane solution of n-butyllithium and allowing the reaction to proceed at −20° C. for 1 hour, 28.4 g (200 mmol) of ethyl trifluoroacetate was added dropwise to the reaction solution at −78° C. The reaction was allowed to proceed for 1 hour at −78° C. and for 1 hour additionally at room temperature. The reaction was quenched with 3N hydrochloric acid, and the reaction solution was extracted with ethyl acetate. The extract was washed with a saturated solution of sodium hydrogen carbonate and brine, successively, and dried with anhydrous magnesium sulfate. After removing ethyl acetate by distillation in vacuo, a furan derivative before purification was obtained.

(b) To a mixture prepared by adding 2.3 g (60 mmol) of sodium borohydride to 100 ml of dry ethanol, the furan derivative before purification obtained by the above reaction was added dropwise at 0° C. in 30 minutes. After the reaction was allowed to proceed for 2 hours at room temperature, ethanol was removed by distillation in vacuo and the reaction was quenched with 3N hydrochloric acid. The reaction mixture was extracted with ethyl acetate. The extract was washed with a saturated solution of sodium hydrogen carbonate and brine, successively, and dried with anhydrous magnesium sulfate. After removing ethyl acetate by distillation in vacuo, the reaction product was distilled in vacuo, and 40.5 g (170 mmol) of an alcohol compound was obtained.

(c) To 300 ml of methylene chloride, 64.1 g (269 mmol) of the alcohol compound obtained by the above reaction in (b) and 27.7 ml (350 mmol) of pyridine were added. To the solution obtained, 27.5 g (350 mmol) of acetyl chloride was added dropwise at 0° C., and the reaction was allowed to proceed at room temperature for 2 hours. Then, the reaction was quenched with 3N hydrochloric acid, and the reaction mixture was extracted with methylene chloride. The extract was washed with a saturated solution of sodium hydrogen carbonate and distilled water, successively, and dried with anhydrous magnesium sulfate. After removing methylene chloride by distillation in vacuo, the reaction product was distilled in vacuo, and 75.1 g (268 mmol) of an ester compound was obtained.

(d) To 1800 ml of distilled water, 58.5 g (209 mmol) of the ester compound obtained by the above reaction was added, and the mixture was stirred in a mini-jar fermenter at 40° C. To this mixture, 30 g of lipase PS was added, and the reaction was allowed to proceed for 10 hours. The reaction was quenched with 3N hydrochloric acid and cooling to 0° C. The reaction mixture was filtered by using celite. The filtrate was extracted with ethyl acetate. The extract was washed with brine, and dried with anhydrous magnesium sulfate. Then, ethyl acetate was removed by distillation in vacuo. After separation and purification by the silica gel column chromatography, 23.2 g (97.4 mmol) of an optically active alcohol compound and 25.6 g (91.4 mmol) of an optically active ester compound were obtained. Optical purity of the alcohol compound obtained was 98.0% e.e.

(e) To a solution prepared by dissolving 25.8 g (108 mmol) of the optically active alcohol compound obtained by the above reaction into 200 ml of methylene chloride, 10.5 g (151 mmol) of imidazole and 23.0 g (151 mmol) of t-butyldimethylsilyl chloride were added at 0° C., and the mixture was stirred for 15 minutes. The reaction was allowed to proceed at room temperature for 16 hours. The reaction was quenched with distilled water, and the reaction solution was extracted with methylene chloride. The extract was washed with distilled water and dried with anhydrous magnesium sulfate. After removing methylene chloride by distillation in vacuo, the product was separated and purified by the column chromatography, and 37.2 g (106 mmol) of a silyl ether compound was obtained.

(f) To 120 ml of acetic acid, 14.1 g (40 mmol) of the silyl ether compound obtained by the above reaction and 23.2 g (60 mmol) of magnesium monoperoxyphthalate were added under nitrogen atmosphere, and the resultant mixture was allowed to react at 80° C. for 12 hours. After removing acetic acid by distillation in vacuo, a saturated solution of sodium hydrogen carbonate was added to the reaction solution. The reaction solution was extracted with ethyl acetate. The extract obtained was washed with brine, and dried with anhydrous magnesium sulfate. After removing ethyl acetate by distillation in vacuo, the reaction product was separated and purified by the column chromatography, and 4.7 g (16 mmol) of a (4S,1'S) butenolide compound and 3.0 g (10 mmol) of a (4R,1'S) butenolide compound were obtained. The starting material in an amount of 4.2 g (12 mmol) was also recovered.

(g) To 40 ml of ethanol, 13.7 g (46 mmol) of the (4S,1'S) and (4R, 1'S) butenolide compounds obtained by the above reaction were dissolved without separating each other. To the resultant solution, 1.4 g of 10% Pd/C (containing 10% by weight of Pd) was added, and the reaction was allowed to proceed at room temperature for 15 hours in hydrogen atmosphere. The reaction solution obtained was filtered, and the solvent was removed from the filtrate by distillation in vacuo. The reaction product was separated and purified by the silica gel column chromatography, and 8.2 g (29 mmol) of a (4S,1'S) butanolide compound and 3.6 g (12 mmol) of (4R,1'S) butanolide compound were obtained.

(h) To a solution prepared by adding 7.5 g (25 mmol) of (4S,1'S) butanolide compound obtained by the above reaction to 40 ml of diethyl ether, was added dropwise 32 ml (30 mmol) of a 0.93 mol/liter n-hexane solution of diisobutyl aluminum hydride at −78° C. under nitrogen atmosphere, and the reaction was allowed to proceed for 3 hours. The reaction was quenched with distilled water. After neutralizing by addition of 1N hydrochloric acid, the reaction solution was extracted with diethyl ether. After washing with brine, the extract was dried with anhydrous magnesium sulfate, and diethyl ether in the extract was removed by distillation in vacuo. The reaction product was then purified by the silica gel column chromatography, and 7.3 g (24 mmol) of a lactol compound was obtained.

(i) To a solution prepared by adding 7.3 g (24 mmol) of the lactol compound obtained by the above reaction to 50 ml of tetrahydrofuran, was added dropwise 10 ml of a tetrahydrofuran solution containing 3.0 g (27 mmol) of potassium t-butoxide at −78° C. under nitrogen atmosphere, and the reaction was allowed to proceed for 3 hours. The reaction was quenched with distilled water. After neutralizing by addition of 1N hydrochloric acid, the reaction solution was extracted with diethyl ether. After washing with brine, the extract was dried with anhydrous magnesium sulfate, and diethyl ether in the extract was removed by distillation in vacuo. The reaction product was then purified by the silica gel column chromatography, and 6.4 g (21 mmol) of the target compound (5S,6S)-tetrahydro-5-t-butyldimethylsiloxy-6-trifluormethyl-2-hydroxypyran was obtained. The compound obtained was found to be a mixture of diastereomers in a ratio by mol of 82:18 by the isomeric fluorine nuclear magnetic resonance method.

Physical properties of the compound obtained are shown in the following.
(1) The (2R,5S,6S) isomer
Molecular formula: $C_{12}H_{23}F_3O_3Si$

| $^1$H-NMR (the proton nuclear magnetic resonance method), δ (ppm) | |
|---|---|
| 0.03 | (s, 6H) |
| 0.85 | (s, 9H) |
| 1.40–2.10 | (m, 4H) |
| 2.90–3.10 | (m, 1H) |
| 3.78 | (dt, J=5.6, 8.9Hz, 1H) |
| 4.11 | (dq, J=9.2, 6.9Hz, 1H) |
| 5.20–5.40 | (m, 1H) |
| $^{19}$F-NMR (the fluorine nuclear magnetic resonance method; reference: CF$_3$COOH), δ(ppm) | |
| 4.90 | (d, J=6.1Hz) |

(2) The (2S,5S,6S) isomer
Molecular formula: $C_{12}H_{23}F_3O_3Si$

| $^1$H-NMR, δ(ppm) | |
|---|---|
| 0.05 | (s, 6H) |
| 0.85 | (s, 9H) |
| 1.40–2.10 | (m, 4H) |
| 3.20–3.40 | (m, 1H) |
| 3.67 | (dq, J=8.8, 6.2Hz, 1H) |
| 3.70–3.90 | (m, 1H) |
| 4.80–5.00 | (m, 1H) |
| $^{19}$F-NMR (reference: CF$_3$COOH), δ(ppm) | |
| 4.80 | (d, J=7.6Hz) |

Reference Example 2

Synthesis of (5S,6S)-tetrahydro-5-t-butyldimethylsiloxy-6-pentafluoroethyl-2-hydroxypyran

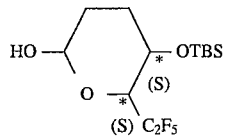

[wherein TBS and * are the same as those described above].

(a) To a solution prepared by adding 19.1 g (281 mmol) of furan to 200 ml of tetrahydrofuran, was added dropwise 187 ml (281 mmol) of a 1.5 mol/liter hexane solution of n-butyllithium at −20° C. under nitrogen atmosphere, and the reaction was allowed to proceed for 1 hour. Then, 30.5 g (281 mmol) of trimethylsilyl chloride was added dropwise to the reaction solution, and the solution was kept stirring at −20° C. for 1 hour. After adding 187 ml (281 mmol) of a 1.5 mol/liter hexane solution of n-butyllithium and allowing the reaction to proceed at −20° C. for 1 hour, 50.0 g (281 mmol) of methyl pentafluoropropionate was added dropwise to the reaction solution at −78° C. The reaction was allowed to proceed for 1 hour at −78° C. and for 1 hour additionally at room temperature. The reaction was quenched with 3N hydrochloric acid, and the reaction solution was extracted with ethyl acetate. The extract was washed with a saturated solution of sodium hydrogen carbonate and brine, successively, and dried with anhydrous magnesium sulfate. After removing ethyl acetate by distillation in vacuo, a furan derivative before purification was obtained.

(b) To a mixture prepared by adding 3.5 g (91 mmol) of sodium borohydride to 200 ml of dry ethanol, the furan derivative before purification obtained above was added dropwise at 0° C. in 30 minutes. After the reaction was allowed to proceed for 2 hours at room temperature, ethanol was removed by distillation in vacuo, and the reaction was quenched with 3N hydrochloric acid. The reaction mixture was extracted with ethyl acetate. The extract was washed with a saturated solution of sodium hydrogen carbonate and brine, successively, and dried with anhydrous magnesium sulfate. After removing ethyl acetate by distillation in vacuo, the reaction product was distilled in vacuo, and 45.3 g (157 mmol) of an alcohol compound was obtained.

(c) To 300 ml of methylene chloride, 41.3 g (143 mmol) of the alcohol compound obtained by the above reaction and 14.7 ml (186 mmol) of pyridine were added. To the solution obtained, 14.5 g (186 mmol) of acetyl chloride was added dropwise at 0° C., and the reaction was allowed to proceed at room temperature for 12 hours. Then, the reaction was quenched with 3N hydrochloric acid, and the reaction mixture was extracted with methylene chloride. The extract was washed with a saturated solution of sodium hydrogen carbonate and distilled water, successively, and dried with anhydrous magnesium sulfate. After removing methylene chloride by distillation in vacuo, the reaction product was distilled in vacuo, and 47.2 g (143 mmol) of an ester compound was obtained.

(d) To 60 ml of distilled water, 2.0 g (6.1 mmol) of the ester compound obtained by the above reaction was added, and the mixture was stirred in a mini-jar fermenter at 40° C. To this mixture, 1.2 g of lipase PS was added, and the reaction was allowed to proceed for 8 days. The reaction was quenched with 3N hydrochloric acid and cooling to 0° C. The reaction mixture was filtered by using celite. The filtrate was extracted with ethyl acetate. The extract was washed with brine, and dried with anhydrous magnesium sulfate. Then, ethyl acetate was removed by distillation in vacuo. After separation and purification by the silica gel column chromatography, 0.47 g (1.6 mmol) of an optically active alcohol compound and 0.73 g (2.2 mmol) of an optically active ester compound were obtained. Optical purity of the alcohol compound obtained was 98.6% e.e.

(e) To a solution prepared by dissolving 1.9 g (6.7 mmol) of the optically active alcohol compound obtained by the above reaction into 15 ml of methylene chloride, 0.6 g (8.0 mmol) of imidazole and 1.2 g (8.0 mmol) of t-butyldimethylsilyl chloride were added at 0° C. and stirred for 15 minutes. The reaction was allowed to proceed at room temperature for 40 hours. The reaction was quenched with distilled water, and the reaction solution was extracted with methylene chloride. The extract was washed with distilled water and dried with anhydrous magnesium sulfate. After removing methylene chloride by distillation in vacuo, the product was separated and purified by the column chromatography, and 2.6 g (6.5 mmol) of a silyl ether compound was obtained.

(f) To 50 ml of acetic acid, 7.3 g (18 mmol) of the silyl ether compound obtained by the above reaction and 25.0 g (65 mmol) of magnesium monoperoxyphthalate were added under nitrogen atmosphere, and the resultant mixture was allowed to react at 50° C. for 24 hours. After removing acetic add by distillation in vacuo, a saturated solution of hydrogen carbonate was added to the reaction solution. The reaction solution was extracted with ethyl acetate. The extract obtained was washed with brine, and dried with anhydrous magnesium sulfate. After removing ethyl acetate by distillation in vacuo, the reaction product was purified by the column chromatography, and 4.5 g (13 mmol) of a mixture of a (4S,1'S) butenolide compound and a (4R,1'S) butenolide compound was obtained.

(g) To 5 ml of ethanol, 0.32 g (1.8 mmol) of the (4S,1'S) and (4R,1'S) butenolide compounds obtained by the above reaction were dissolved without separating each other. To the resultant solution, 0.04 g of 10% Pd/C (containing 10% by weight of Pd) was added, and the reaction was allowed to proceed at room temperature for 20 hours in hydrogen atmosphere. The reaction solution obtained was filtered, and the solvent was removed from the filtrate by distillation in vacuo. The reaction product was separated and purified by the silica gel column chromatography, and 0.13 g (0.7 mmol) of a (4S,1'S) butanolide compound and 0.13 g (0.7 mmol) of (4R,1'S) butanolide compound were obtained.

(h) To a solution prepared by adding 1.6 g (4.7 mmol) of (4S,1'S) butanolide compound obtained by the above reaction to 10 ml of diethyl ether, was added dropwise 6.0 ml (5.6 mmol) of a 0.93 mol/liter n-hexane solution of diisobutyl aluminum hydride under nitrogen atmosphere, and the reaction was allowed to proceed for 5 hours. The reaction was quenched with distilled water. After neutralizing by addition of 1N hydrochloric acid, the reaction solution was extracted with diethyl ether. After washing with brine, the extract was dried with anhydrous magnesium sulfate, and diethyl ether in the extract was removed by distillation in vacuo. The reaction product was then purified by the silica gel column chromatography, and 1.5 g (4.3 mmol) of a lactol compound was obtained.

(i) To a solution prepared by adding 1.5 g (4.3 mmol) of the lactol compound obtained by the above reaction to 10 ml of tetrahydrofuran, was added dropwise 5 ml of a tetrahydrofuran solution containing 0.5 g (5.0 mmol) of potassium t-butoxide at −78° C. under nitrogen atmosphere, and the reaction was allowed to proceed for 6 hours. The reaction was quenched with distilled water. After neutralizing by addition of 1N hydrochloric acid, the reaction solution was extracted with diethyl ether. After washing with brine, the extract was dried with anhydrous magnesium sulfate, and diethyl ether in the extract was removed by distillation in vacuo. The reaction product was then purified by the silica gel column chromatography, and 1.4 g (4.0 mmol) of the target compound (5S,6S)-tetrahydro-5-t-butyldimethylsiloxy-6-pentafluoroethyl-2-hydroxypyran was obtained.

EXAMPLE 1

Synthesis of
(2S,5S,6S)-tetrahydro-6-trifluoromethyl-
2-(4"-hexyloxybiphenyl-4'-carbonyloxy)-
5-trimethylsiloxypyran

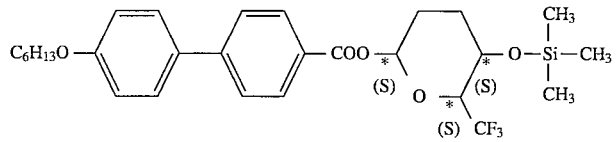

(a) To 5 ml of a toluene solution containing 1.43 g (4.5 mmol) of 4'-hexyloxy-4-biphenylcarboxylic acid chloride and 0.90 g (3.0 mmol) of (5S,6S)-tetrahydro-5-t-butyldimethylsiloxy-6-trifluoromethyl-2-hydroxypyran obtained in Reference Example 1, 2 ml of anhydrous pyridine was added, and the reaction was allowed to proceed at room temperature for 20 hours. The reaction was quenched with distilled water to the reaction solution, and the reaction solution was extracted with diethyl ether. The extract was washed with brine, and dried with anhydrous magnesium sulfate. Then, diethyl ether was removed by distillation in vacuo. After separation and purification by the silica gel column chromatography, 1.26 g (2.2 mmol) of an ester compound was obtained.

(b) To 10 ml of tetrahydrofuran, 1.26 g of the ester compound obtained in (a) was dissolved. To the resultant solution, 1.0 ml of a 1.0 mol/liter tetrahydrofuran solution of tetra-n-butylammonium fluoride was added. The reaction was allowed to proceed at 0° C. for 1 hour and then at room temperature for 6 hours. The reaction was quenched with distilled water to the reaction solution, and the reaction solution was extracted with diethyl ether. The extract was washed with brine, and dried with anhydrous magnesium sulfate. After removing diethyl ether by distillation in vacuo, the product was separated and purified by the silica gel column chromatography, and 0.09 g (0.2 mmol) of an alcohol compound having asymmetric carbon atoms of (2R,5S,6S) and 0.73 g (1.6 mmol) of an alcohol compound having asymmetric carbon atoms of (2S,5S,6S) were obtained.

(c) To 10 ml of methylene chloride, 0.70 g (1.5 mmol) of the alcohol compound having asymmetric carbon atoms of (2S,5S,6S) obtained in (b) was dissolved. To the resultant solution, 0.4 ml (3.0 mmol) of chlorotrimethylsilane and 0.20 g (3.0 mmol) of imidazole were added successively, and the reaction was allowed to proceed at 0° C. for 1 hour and then at room temperature for 14 hours. The reaction was quenched with distilled water to the reaction solution, and the reaction solution was extracted with methylene chloride. The extract was washed with distilled water, and dried with anhydrous magnesium sulfate. After removing methylene chloride by distillation in vacuo, the reaction product was separated and purified by the silica gel column chromatography, and 0.48 g (0.9 mmol) of the target compound (2S,5S,6S)-tetrahydro-6-trifluoromethyl-2-(4''-hexyloxybiphenyl-4'-carbonyloxy)-5-trimethylsiloxypyran was obtained.

Physical properties of the compound obtained are shown in the following.

Molecular formula: $C_{28}H_{37}F_3O_5Si$

| $^1$H-NMR (the proton nuclear magnetic resonance method), δ (ppm) | |
|---|---|
| 0.15 | (s, 9H) |
| 0.91 | (t, J=6.9Hz, 3H) |
| 1.27–1.58 | (m, 6H) |
| 1.67–2.28 | (m, 6H) |
| 3.82–3.97 | (m, 2H) |
| 4.00 | (t, J=6.6Hz, 2H) |
| 6.06 | (dd, J=2.2, 8.1Hz, 1H) |
| 6.98 | (d, J=8.7Hz, 2H) |
| 7.56 | (d, J=8.7Hz, 2H) |
| 7.62 | (d, J=8.4Hz, 2H) |
| 8.10 | (d, J=8.3Hz, 2H) |
| $^{19}$F-NMR (the fluorine nuclear magnetic resonance method; reference: CFCl$_3$), δ(ppm) | |
| −74.73 | (d, J=6.3Hz) |
| IR (cm$^{-1}$) | |
| 1740, 1600, 1495, 1260, 1180, 1085 | |
| $[\alpha]_D^{26}$=+13.0°(c(concentration)=1.01; solvent: chloroform) | |
| mass analysis m/e(M$^+$) | |
| calculated for $C_{28}H_{37}F_3O_5Si$ | 538.2363 |
| found | 538.2349 |

EXAMPLE 2

Synthesis of (2S,5S,6S)-tetrahydro-6-trifluoromethyl-2-(4''-hexyloxybiphenyl-4'-carbonyloxy)-5-tert-butyldimethylsiloxypyran

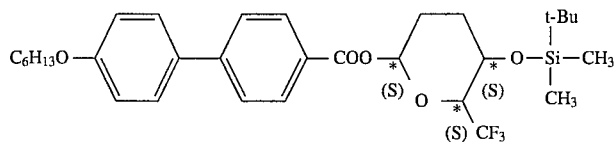

wherein t-Bu represents tert-butyl group. This representation is used similarly hereinafter.

The same procedures as those in Example 1 (c) were conducted by using 0.47 g (1.0 mmol) of the alcohol compound having asymmetric carbon atoms of (2S,5S,6S) obtained in Example 1 (b) and 0.23 g (1.5 mmol) of chloro-tert-butyldimethylsilane, and 0.51 g (0.9 mmol) of the target compound (2S,5S,6S)-tetrahydro-6-trifluoromethyl-2-(4''-hexyloxybiphenyl-4'-carbonyloxy)-5-tert-butyldimethylsiloxypyran was obtained.

Physical properties of the compound obtained are shown in the following.

Molecular formula: $C_{31}H_{43}F_3O_5Si$

| $^1$H-NMR, δ(ppm) | |
|---|---|
| 0.09 | (s, 3H) |
| 0.11 | (s, 3H) |
| 0.82–1.00 | (m, 12H) |
| 1.26–1.55 | (m, 6H) |
| 1.63–2.29 | (m, 6H) |
| 3.85–4.00 | (m, 2H) |
| 4.01 | (t, J=6.6Hz, 2H) |
| 6.08 | (dd, J=2.4, 7.8Hz, 1H) |
| 6.98 | (d, J=8.4Hz, 2H) |
| 7.56 | (d, J=8.7Hz, 2H) |
| 7.62 | (d, J=8.4Hz, 2H) |
| 8.10 | (d, J=8.4Hz, 2H) |
| $^{19}$F-NMR (reference: CFCl$_3$), δ(ppm) | |
| −74.57 | (d, J=6.4Hz) |
| IR (cm$^{-1}$) | |
| 1735, 1600, 1250, 1175, 1080 | |
| $[\alpha]_D^{26}$=+18.2°(c(concentration)=1.02; solvent: chloroform) | |
| mass analysis m/e(M$^+$) | |
| calculated for $C_{31}H_{43}F_3O_5Si$ | 580.2832 |
| found | 580.2814 |

EXAMPLE 3

Synthesis of (2S,5S,6S)-tetrahydro-6-trifluoromethyl-2-(4''-hexyloxybiphenyl-4'-carbonyloxy)-5-triethylsiloxypyran

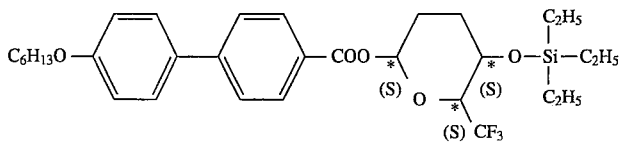

The same procedures as those in Example 1 (c) were conducted by using 0.18 g (0.4 mmol) of the alcohol compound having asymmetric carbon atoms of (2S,5S,6S) obtained in Example 1 (b) and 0.13 ml (0.8 mmol) of chlorotriethylsilane, and 0.20 g (0.3 mmol) of the target compound (2S,5S,6S)-tetrahydro-6-trifluoromethyl-2-(4''- hexyloxybiphenyl-4'-carbonyloxy)-5-triethylsiloxypyran was obtained.

Physical properties of the compound obtained are shown in the following.

Molecular formula: $C_{31}H_{43}F_3O_5Si$

| $^1$H-NMR, δ(ppm) | |
|---|---|
| 0.62 | (q, J=7.8Hz, 6H) |
| 0.88–0.97 | (m, 3H) |
| 0.97 | (t, J=7.8Hz, 9H) |
| 1.27–1.58 | (m, 6H) |
| 1.67–2.29 | (m, 6H) |
| 3.87–3.99 | (m, 2H) |
| 4.00 | (t, J=6.5Hz, 2H) |
| 6.09 | (dd, J=2.2, 7.5Hz, 1H) |
| 6.98 | (d, J=8.7Hz, 2H) |
| 7.55 | (d, J=8.7Hz, 2H) |
| 7.62 | (d, J=8.4Hz, 2H) |
| 8.10 | (d, J=8.4Hz, 2H) |
| $^{19}$F-NMR (reference: CFCl$_3$), δ(ppm) | |
| −74.66 | (d, J=6.7Hz) |
| IR (cm$^{-1}$) | |
| 1735, 1600, 1490, 1260, 1175, 1080 | |
| $[\alpha]_D^{24}$=+14.9°(c(concentration)=1.08; solvent: chloroform) | |
| mass analysis m/e(M$^+$) | |
| calculated for $C_{31}H_{43}F_3O_5Si$ | 580.2832 |
| found | 580.2841 |

EXAMPLE 4

Synthesis of
(2S,5S,6S)-tetrahydro-6-trifluoromethyl-2-(4"-hexyloxybiphenyl-4'-carbonyloxy)-5-tripropylsiloxypyran

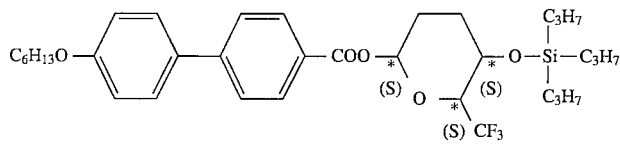

The same procedures as those in Example 1 (c) were conducted by using 0.93 g (2.0 mmol) of the alcohol compound having asymmetric carbon atoms of (2S,5S,6S) obtained in Example 1 (b) and 0.85 ml (4.0 mmol) of chlorotripropylsilane, and 0.94 g (1.5 mmol) of the target compound (2S,5S,6S)-tetrahydro-6-trifluoromethyl-2-(4"-hexyloxybiphenyl-4'-carbonyloxy)-5-tripropylsiloxypyran was obtained.

Physical properties of the compound obtained are shown in the following.

Molecular formula: $C_{34}H_{49}F_3O_5Si$

| H-NMR, δ(ppm) | |
|---|---|
| 0.54–0.69 | (m, 6H) |
| 0.85–0.94 | (m, 6H) |
| 0.98 | (t, J=7.3Hz, 9H) |
| 1.24–1.53 | (m, 12H) |
| 1.67–2.28 | (m, 6H) |
| 3.83–3.97 | (m, 2H) |
| 4.01 | (t, J=6.5Hz, 2H) |
| 6.10 | (dd, J=2.1, 7.6Hz, 1H) |
| 6.99 | (d, J=8.6Hz, 2H) |
| 7.56 | (d, J=8.5Hz, 2H) |
| 7.62 | (d, J=8.2Hz, 2H) |
| 8.10 | (d, J=8.2Hz, 2H) |
| $^{19}$F-NMR (reference: CFCl$_3$), δ(ppm) | |
| −74.64 | (d, J=6.7Hz) |
| IR (cm$^{-1}$) | |
| 1740, 1605, 1500, 1270, 1200, 1185, 1080 | |
| $[\alpha]_D^{26}$=+14.8°(c(concentration)=1.06; solvent: chloroform) | |
| mass analysis m/e(M$^+$) | |
| calculated for $C_{34}H_{49}F_3O_5Si$ | 622.3302 |
| found | 622.3285 |

EXAMPLE 5

Synthesis of
(2R,5S,6S)-tetrahydro-6-trifluoromethyl-2-(4"-hexyloxybiphenyl-4'-carbonyloxy)-5-tert-butyldimethylsiloxypyran

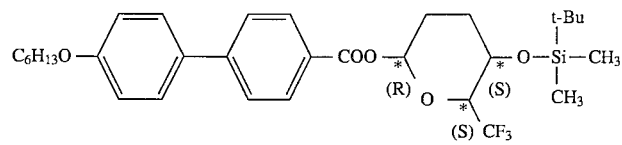

The same procedures as those in Example 1 (c) were conducted by using 0.33 g (0.7 mmol) of the alcohol compound having asymmetric carbon atoms of (2R,5S,6S) obtained in Example 1 (b) and 0.16 g (1.1 mmol) of chloro-tert-butyldimethylsilane, and 0.37 g (0.6 mmol) of the target compound (2R,5S,6S)-tetrahydro-6-trifluoromethyl-2-(4"-hexyloxybiphenyl-4'-carbonyloxy)-5-tert-butyldimethylsiloxypyran was obtained.

Physical properties of the compound obtained are shown in the following.

Molecular formula: $C_{31}H_{43}F_3O_5Si$ $^1$H-NMR, δ(ppm)

| | |
|---|---|
| 0.10 | (s, 3H) |
| 0.12 | (s, 3H) |
| 0.81~1.07 | (m, 12H) |
| 1.18~1.61 | (m, 6H) |
| 1.74~2.18 | (m, 6H) |
| 3.88~4.17 | (m, 2H) |
| 4.01 | (t, J=6.5Hz, 2H) |
| 6.40~6.48 | (m, 1H) |
| 7.00 | (d, J=8.7Hz, 2H) |
| 7.57 | (d, J=8.7Hz, 2H) |
| 7.66 | (d, J=8.3HZ, 2H) |
| 8.11 | (d, J=8.3Hz, 2H) |

$^{19}$F-NMR (reference: $CFCl_3$), δ(ppm)

| | |
|---|---|
| −74.57 | (d, J=6.2Hz) |

$[\alpha]_D^{24}$=+49.0°(c(concentration)=1.04; solvent: chloroform)

mass analysis m/e(M$^+$)

| | |
|---|---|
| calculated for $C_{31}H_{43}F_3O_5Si$ | 580.2832 |
| found | 580.2861 |

EXAMPLE 6

Synthesis of
(2R,5S,6S)-tetrahydro-6-trifluoromethyl-2-(4"-hexyloxybiphenyl-4'-carbonyloxy)-
5-triethylsiloxypyran

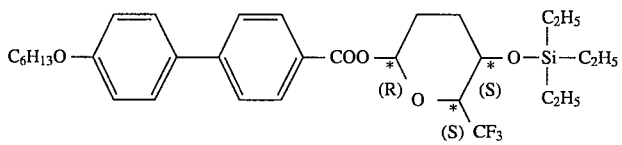

The same procedures as those in Example 1 (c) were conducted by using 0.16 g (0.3 mmol) of the alcohol compound having asymmetric carbon atoms of (2R,5S,6S) obtained in Example 1 (b) and 0.1 ml (0.7 mmol) of chlorotriethylsilane, and 0.17 g (0.3 mmol) of the target compound (2R,5S,6S)-tetrahydro-6-trifluoromethyl-2-(4"-hexyloxybiphenyl-4'-carbonyloxy)-5-triethylsiloxypyran was obtained.

Physical properties of the compound obtained are shown in the following.

Molecular formula: $C_{31}H_{43}F_3O_5Si$ $^1$H-NMR, δ(ppm)

| | |
|---|---|
| 0.65 | (q, J=7.9Hz, 6H) |
| 0.83~1.07 | (m, 12H) |
| 1.20~1.58 | (m, 6H) |
| 1.73~2.12 | (m, 6H) |
| 3.88~4.18 | (m, 2H) |
| 4.01 | (t, J=6.6Hz, 2H) |
| 6.41~6.48 | (m, 1H) |
| 7.00 | (d, J=8.7Hz, 2H) |
| 7.57 | (d, J=8.7Hz, 2H) |
| 7.65 | (d, J=8.3Hz, 2H) |
| 8.10 | (d, J=8.3Hz, 2H) |

$^{19}$F-NMR (reference: $CFCl_3$), δ(ppm)

| | |
|---|---|
| −74.70 | (d, J=6.2Hz) |

$[\alpha]_D^{28}$=+49.6°(c (concentration)=0.84; solvent: chloroform)

mass analysis m/e(M$^+$)

| | |
|---|---|
| calculated for $C_{31}H_{43}F_3O_5Si$ | 580.2832 |
| found | 580.2836 |

EXAMPLE 7

Synthesis of
(2R,5S,6S)-tetrahydro-6-trifluoromethyl-2-
(4"-hexyloxybiphenyl-4'-carbonyloxy)-
5-tripropylsiloxypyran

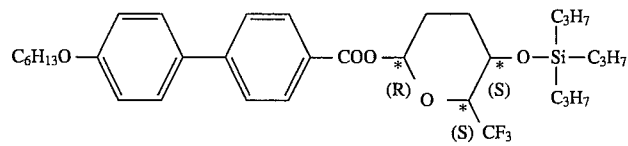

The same procedures as those in Example 1 (c) were conducted by using 0.16 g (0.3 mmol) of the alcohol compound having asymmetric carbon atoms of (2R,5S,6S) obtained in Example 1 (b) and 0.2 ml (0.7 mmol) of chlorotripropylsilane, and 0.18 g (0.3 mmol) of the target compound (2R,5S,6S)-tetrahydro-6-trifluoromethyl-2-(4"-hexyloxybiphenyl-4'-carbonyloxy)-5-tripropylsiloxypyran was obtained.

Physical properties of the compound obtained are shown in the following.

Molecular formula: $C_{34}H_{49}F_3O_5Si$ $^1$H-NMR, δ(ppm)

| | |
|---|---|
| 0.57~0.72 | (m, 6H) |
| 0.85~0.99 | (m, 3H) |
| 0.98 | (t, J=7.2Hz, 9H) |
| 1.25~1.58 | (m, 12H) |

| | |
|---|---|
| 1.75~2.12 | (m, 6H) |
| 3.89~4.17 | (m, 2H) |
| 4.01 | (t, J=6.6Hz, 2H) |
| 6.40~6.47 | (m, 1H) |
| 7.00 | (d, J=8.8Hz, 2H) |
| 7.57 | (d, J=8.8Hz, 2H) |
| 7.65 | (d, J=8.4Hz, 2H) |
| 8.10 | (d, J=8.4Hz, 2H) |
| $^{19}$F-NMR (reference: CFCl$_3$), δ(ppm) | |
| −74.69 | (d, J=6.2Hz) |
| $[α]_D^{25}$=+49.5°(c(concentration)=1.05; solvent: chloroform) | |
| mass analysis m/e(M$^+$) | |
| calculated for C$_{34}$H$_{49}$F$_3$O$_5$Si | 622.3302 |
| found | 622.3289 |

EXAMPLE 8

Synthesis of (2S,5R,6R)-tetrahydro-6-trifluoromethyl-5-(4''-hexyloxybiphenyl-4'-carbonyloxy)-2-tert-butyldimethylsiloxypyran

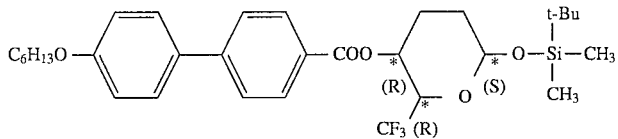

(a) To 10 ml of a diethyl ether solution containing 1.00 g (3.3 mmol) of (5R,6R)-tetrahydro-5-tert-butyldimethylsiloxy-6-trifluoromethyl-2-hydroxypyran obtained by the same procedures as those in Reference Example 1 and 0.45 ml (5.0 mmol) of dihydropyran, 0.1 g of paratoluenesulfonic acid was added, and the reaction was allowed to proceed at room temperature for 20 hours. The reaction was quenched with distilled water to the reaction solution, and the reaction solution was extracted with diethyl ether. The extract was washed with brine, and then dried with anhydrous magnesium sulfate. After removing diethyl ether by distillation in vacuo, the reaction product was purified by the silica gel column chromatography, and 1.04 g (2.7 mmol) of an acetal compound was obtained.

(b) The same procedures as those in Example 1 (b) were conducted by using 1.04 g (2.7 mmol) of the acetal compound obtained in (a), and 0.49 g (1.8 mmol) of an alcohol compound was obtained.

(c) The same procedures as those in Example 1 (a) were conducted by using 0.49 g (1.8 mmol) of the alcohol compound obtained in (b) and 0.62 g (2.0 mmol) of 4°-hexyloxy-4-biphenylcarboxylic acid chloride, and 0.74 g (1.3 mmol) of an ester compound was obtained.

(d) To 10 ml of diethyl ether, 0.74 g (1.3 mmol) of the ester compound obtained in (c) was dissolved, and 0.1 g of para-toluenesulfonic acid was added to the resultant solution. The reaction was allowed to proceed at room temperature for 5 days. The reaction was quenched with distilled water to the reaction solution, and the reaction solution was extracted with diethyl ether. The extract was washed with brine and then dried with anhydrous magnesium sulfate. After removing diethyl ether by distillation in vacuo, the reaction product was separated and purified by the silica gel column chromatography, and 0.40 g (0.9 mmol) of a hemiacetal compound was obtained.

(e) To 10 ml of methylene chloride, 0.40 g (0.9 mmol) of the hemiacetal compound obtained in (d) was dissolved. To the resultant solution, 0.19 g (1.3 mmol) of chloro-tert-butyldimethylsilane and 0.09 g (1.3 mmol) of imidazole were added at 0° C., and mixed by stirring for 1 hour. Then, the reaction was allowed to proceed at room temperature for hours. The reaction was quenched with distilled water, and the reaction solution was extracted with methylene chloride. The extract was washed with distilled water, and dried with anhydrous magnesium sulfate. After removing methylene chloride by distillation in vacuo, the reaction product was separated and purified by the column chromatography, and 0.31 g (0.5 mmol) of the target compound (2S,5R,6R)-tetrahydro-6-trifluoromethyl-5-(4''-hexyloxybiphenyl-4'-carbonyloxy)-2-tert-butyldimethylsiloxypyran was obtained.

Physical properties of the compound obtained are shown in the following.

Molecular formula: C$_{31}$H$_{43}$F$_3$O$_5$Si

| $^1$H-NMR, δ(ppm) | |
|---|---|
| 0.14 | (s, 3H) |
| 0.15 | (s, 3H) |
| 0.82–0.99 | (m, 12H) |
| 1.28–1.53 | (m, 6H) |
| 1.66–2.01 | (m, 5H) |
| 2.35–2.46 | (m, 1H) |
| 4.00 | (t, J=6.6Hz, 2H) |
| 4.01–4.12 | (m, 1H) |
| 4.94 | (dd, J=2.1, 8.2Hz, 1H) |
| 5.17–5.25 | (m, 1H) |
| 6.98 | (d, J=8.8Hz, 2H) |
| 7.55 | (d, J=8.8Hz, 2H) |
| 7.61 | (d, J=8.5Hz, 2H) |
| 8.03 | (d, J=8.4Hz, 2H) |
| $^{19}$F-NMR (reference: CFCl$_3$), δ(ppm) | |
| −75.84 | (d, J=6.1Hz) |
| $[α]_D^{23}$=−5.8°(c(concentration)=1.06; solvent: chloroform) | |
| mass analysis m/e(M$^+$) | |
| calculated for C$_{31}$H$_{43}$F$_3$O$_5$Si | 580.2832 |
| found | 580.2830 |

EXAMPLE 9

Synthesis of (2S,5S,6S)-tetrahydro-6-pentafluoroethyl-2-(4''-hexyloxybiphenyl-4'-carbonyloxy)-5-tert-butyldimethylsiloxypyran

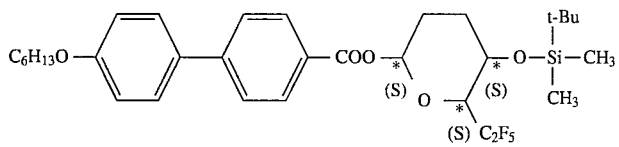

To 10 ml of a toluene solution containing 0.77 g (2.4 mmol) of 4'-hexyloxy-4-biphenylcarboxylic acid chloride and 0.66 g (1.9 mmol) of (5S,6S)-tetrahydro-5-tert-butyldimethylsiloxy-6-pentafluoroethyl-2-hydroxypyran obtained in Reference Example 2, 0.3 ml (2.3 mmol) of triethylamine was added, and the reaction was allowed to proceed at room temperature for 20 hours. The reaction was quenched with distilled water to the reaction solution, and the reaction solution was extracted with diethyl ether. The extract was washed with brine, and then dried with anhydrous magnesium sulfate. After removing diethyl ether by distillation in vacuo, the reaction product was purified by the silica gel column chromatography, and 0.52 g (0.8 mmol) of the target compound (2S,5S,6S)-tetrahydro-6-pentafluoroethyl-2-(4''-hexyloxybiphenyl-4'-carbonyloxy)-5-tert-butyldimethylsiloxypyran was obtained.

Physical properties of the compound obtained are shown in the following.

Molecular formula: $C_{32}H_{43}F_5O_5Si$

| $^1$H-NMR, δ(ppm) | |
|---|---|
| 0.10 | (s, 3H) |
| 0.12 | (s, 3H) |
| 0.81–1.08 | (m, 12H) |
| 1.23–1.58 | (m, 6H) |
| 1.69–1.99 | (m, 4H) |
| 2.08–2.31 | (m, 2H) |
| 3.98–4.17 | (m, 2H) |
| 4.00 | (t, J=6.5Hz, 2H) |
| 6.06 | (dd, J=2.4, 7.8Hz, 1H) |
| 6.98 | (d, J=8.7Hz, 2H) |
| 7.56 | (d, J=8.7Hz, 2H) |
| 7.62 | (d, J=8.3Hz, 2H) |
| 8.09 | (d, J=8.3Hz, 2H) |
| $^{19}$F-NMR(reference: $CFCl_3$), δ(ppm) | |
| −82.36 | (s, 3F) |
| −117.85 | (dd, J=5.2, 277.9Hz, 1F) |
| −129.74 | (dd, J=20.1, 278.0Hz, 1F) |
| $[α]_D^{26}$=+22.5°(c(concentration)=0.96; solvent: chloroform) | |
| mass analysis m/e(M$^+$) | |
| calculated for $C_{32}H_{43}F_5O_5Si$ | 630.2800 |
| found | 630.2792 |

EXAMPLE 10

Synthesis of (2R,5R,6R)-tetrahydro-6-trifluoromethyl-2-(4''-nonyloxybiphenyl-4'-carbonyloxy)-5-tert-butyldimethylsiloxypyran

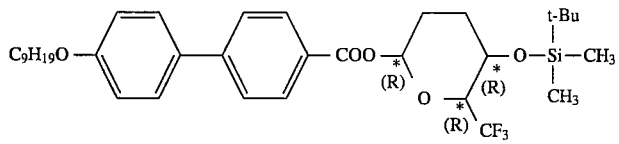

The same procedures as those in Example 9 were conducted by using 0.79 g (2.2 mmol) of 4'-nonyloxy-4-biphenylcarboxylic acid chloride and 0.50 g (1.7 mmol) of (5R,6R)-tetrahydro-5-tert-butyldimethylsiloxy-6-trifluoromethyl-2-hydroxypyran obtained by the same procedures as those in Reference Example 1, and 0.51 g (0.8 mmol) of the target compound (2R,5R,6R)-tetrahydro-6-trifluoromethyl-2-(4''-nonyloxybiphenyl-4'-carbonyloxy)-5-tert-butyldimethylsiloxypyran was obtained.

Physical properties of the compound obtained are shown in the following.

Molecular formula: $C_{34}H_{49}F_3O_5Si$

| $^1$H-NMR, δ(ppm) | |
|---|---|
| 0.09 | (s, 3H) |
| 0.11 | (s, 3H) |
| 0.88–0.96 | (m, 12H) |
| 1.23–1.56 | (m, 12H) |
| 1.70–2.28 | (m, 6H) |
| 3.83–3.97 | (m, 2H) |
| 4.00 | (t, J=6.5Hz, 2H) |
| 6.08 | (dd, J=2.4, 7.8Hz, 1H) |
| 6.98 | (d, J=8.8Hz, 2H) |
| 7.56 | (d, J=8.8Hz, 2H) |
| 7.62 | (d, J=8.5Hz, 2H) |
| 8.10 | (d, J=8.4Hz, 2H) |
| $^{19}$F-NMR(reference: $CFCl_3$), δ(ppm) | |
| −74.57 | (d, J=6.4Hz) |
| $[α]_D^{26}$=−16.7°(c(concentration)=1.00; solvent: chloroform) | |
| mass analysis m/e(M$^+$) | |
| calculated for $C_{34}H_{49}F_3O_5Si$ | 622.3302 |
| found | 622.3297 |

EXAMPLE 11

Synthesis of (2R,5R,6R)-tetrahydro-6-trifluoromethyl-2-(4''-decyloxybiphenyl-4'-carbonyloxy)-5-tert-butyldimethylsiloxypyran

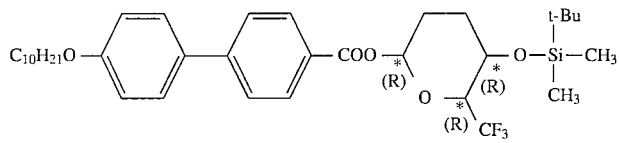

The same procedures as those in Example 9 were conducted by using 1.51 g (4.0 mmol) of 4'-decyloxy-4-biphenylcarboxylic acid chloride and 1.00 g (3.3 mmol) of (5R,6R)-tetrahydro-5-tert-butyldimethylsiloxy-6-trifluoromethyl-2-hydroxypyran obtained by the same procedures as those in Reference Example 1, and 1.55 g (2.4 mmol) of the target compound (2R,5R,6R)-tetrahydro-6-trifluoromethyl-2-(4''-decyloxybiphenyl-4'-carbonyloxy)-5-tert-butyldimethylsiloxypyran was obtained.

Physical properties of the compound obtained are shown in the following.

Molecular formula: $C_{35}H_{51}F_3O_5Si$

| $^1$H-NMR, δ(ppm) | |
|---|---|
| 0.09 | (s, 3H) |
| 0.11 | (s, 3H) |
| 0.83–0.92 | (m, 12H) |
| 1.20–1.57 | (m, 14H) |
| 1.65–2.28 | (m, 6H) |
| 3.88–4.02 | (m, 2H) |
| 4.00 | (t, J=6.5Hz, 2H) |
| 6.08 | (dd, J=2.4, 7.8Hz, 1H) |
| 6.98 | (d, J=8.7Hz, 2H |
| 7.56 | (d, J=8.8Hz, 2H) |
| 7.62 | (d, J=8.5Hz, 2H) |
| 8.10 | (d, J=8.4Hz, 2H) |
| $^{19}$F-NMR(reference: CFCl$_3$), δ(ppm) | |
| −74.57 | (d, J=6.5Hz) |
| $[α]_D^{24}$=−16.3°(c(concentration)=1.03; solvent: chloroform) | |
| mass analysis m/e(M$^+$) | |
| calculated for $C_{35}H_{51}F_3O_5Si$ | 636.3458 |
| found | 636.3444 |

EXAMPLE 12

Synthesis of (2R,5R,6R)-tetrahydro-6-trifluoromethyl-2-(4''-undecyloxybiphenyl-4'-carbonyloxy)-5-tert-butyldimethylsiloxypyran

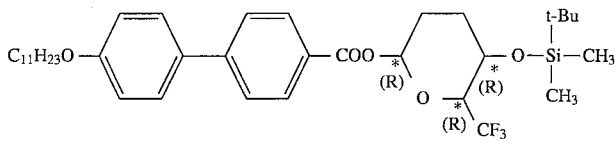

The same procedures as those in Example 9 were conducted by using 0.85 g (2.2 mmol) of 4'-undecyloxy-4-biphenylcarboxylic acid chloride and 0.50 g (1.7 mmol) of (5R,6R)-tetrahydro-5-tert-butyldimethylsiloxy-6-trifluoromethyl-2-hydroxypyran obtained by the same procedures as those in Reference Example 1, and 0.65 g (1.0 mmol) of the target compound (2R,5R,6R)-tetrahydro-6-trifluoromethyl-2-(4''-undecyloxybiphenyl-4'-carbonyloxy)-5-tert-butyldimethylsiloxypyran was obtained.

Physical properties of the compound obtained are shown in the following.

Molecular formula: $C_{36}H_{53}F_3O_5Si$

| $^1$H-NMR, δ(ppm) | |
|---|---|
| 0.09 | (s, 3H) |
| 0.11 | (s, 3H) |
| 0.82–0.96 | (m, 12H) |
| 1.22–1.55 | (m, 16H) |
| 1.68–2.27 | (m, 6H) |
| 3.83–3.99 | (m, 2H) |
| 4.00 | (t, J=6.6Hz, 2H) |
| 6.08 | (dd, J=2.3, 7.8Hz, 1H) |
| 6.98 | (d, J=8.7Hz, 2H) |
| 7.56 | (d, J=8.8Hz, 2H) |
| 7.62 | (d, J=8.4Hz, 2H) |
| 8.10 | (d, J=8.4Hz, 2H) |
| $^{19}$F-NMR(reference: CFCl$_3$), δ(ppm) | |
| −74.57 | (d, J=6.5Hz) |
| $[α]_D^{25}$=−16.1°(c(concentration)=1.03; solvent: chloroform) | |
| mass analysis m/e(M$^+$) | |
| calculated for $C_{36}H_{53}F_3O_5Si$ | 650.3615 |
| found | 650.3598 |

EXAMPLE 13

Synthesis of (2R,5R,6R)-tetrahydro-6-trifluoromethyl-2-(4''-decyloxybiphenyl-4'-carbonyloxy)-5-tripropylsiloxypyran

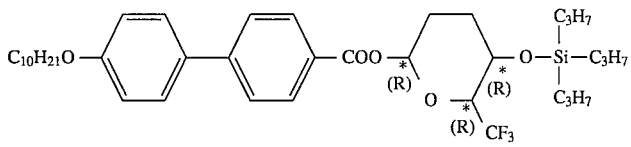

(a) The same procedures as those in Example 1 (b) were conducted by using 1.28 g (2.0 mmol) of the ester compound obtained in Example 11, and 0.56 g (1.1 mmol) of an alcohol compound having asymmetric carbon atoms of (2R,5R,6R) and 0.37 g (0.7 mmol) of an alcohol compound having asymmetric carbon atoms of (2S,5R,6R) were obtained.

(b) The same procedures as those in Example 4 were conducted by using 0.56 g (1.1 mmol) of the alcohol compound having asymmetric carbon atoms of (2R,5R,6R) obtained in (a) and 0.31 g (1.6 mmol) of chlorotripropylsilane, and 0.65 g (1.0 mmol) of the target compound (2R,5R,6R)-tetrahydro-6-trifluoromethyl-2-(4''-decyloxybiphenyl-4'-carbonyloxy)-5-tripropylsiloxypyran was obtained.

Physical properties of the compound obtained are shown in the following.

Molecular formula: $C_{38}H_{57}F_3O_5Si$

| $^1$H-NMR, δ(ppm) | |
|---|---|
| 0.59–0.70 | (m, 6H) |
| 0.88 | (t, J=6.3Hz, 3H) |
| 0.98 | (t, J=7.2Hz, 9H) |
| 1.19–1.55 | (m, 20H) |
| 1.65–2.28 | (m, 6H) |
| 3.86–4.01 | (m, 2H) |
| 4.00 | (t, J=6.5Hz, 2H) |
| 6.10 | (dd, J=2.3, 7.4Hz, 1H) |
| 6.98 | (d, J=8.8Hz, 2H) |
| 7.56 | (d, J=8.7Hz, 2H) |
| 7.62 | (d, J=8.4Hz, 2H) |
| 8.10 | (d, J=8.4Hz, 2H) |
| $^{19}$F-NMR(reference: CFCl$_3$), δ(ppm) | |
| –74.61 | (d, J=6.7Hz) |
| $[\alpha]_D^{25}$=–13.2°(c(concentration)=1.01; solvent: chloroform) | |
| mass analysis m/e(M$^+$) | |
| calauclated for $C_{38}H_{57}F_3O_5Si$ | 678.3928 |
| found | 678.3905 |

EXAMPLE 14

Synthesis of (2R,5R,6R)-tetrahydro-6-trifluoromethyl-2-[4-(5'-heptyl-2'-pyrimidinyl)phenyl-1-carbonyloxy]-5-tert-butyldimethylsiloxypyran

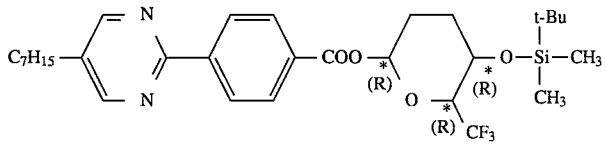

The same procedures as those in Example 9 were conducted by using 0.70 g (2.2 mmol) of 4-(5'-heptyl-2'-pyrimidinyl)benzoic acid chloride and 0.60 g (2.0 mmol) of (5R,6R)-tetrahydro-5-tert-butyldimethylsiloxy-6-trifluoromethyl-2-hydroxypyran obtained by the same procedures as those in Reference Example 1, and 1.0 g (1.7 mmol) of the target compound (2R,5R,6R)-tetrahydro-6-trifluoromethyl-2-[4-(5'-heptyl-2'-pyridinyl)phenyl-1-carbonyloxy]-5-tert-butyldimethylsiloxypyran was obtained.

Physical properties of the compound obtained are shown in the following.

Molecular formula: $C_{30}H_{43}F_3O_4N_2Si$

| $^1$H-NMR, δ(ppm) | |
|---|---|
| 0.09 | (s, 3H) |
| 0.11 | (s, 3H) |
| 0.82–0.97 | (m, 12H) |
| 1.19–1.42 | (m, 8H) |
| 1.65–2.28 | (m, 6H) |
| 2.65 | (t, J=7.6Hz, 2H) |
| 3.84–4.00 | (m, 2H) |
| 6.09 | (dd, J=2.3, 7.9Hz, 1H) |
| 8.17 | (d, J=8.5Hz, 2H) |
| 8.50 | (d, J=8.5Hz, 2H) |
| 8.66 | (s, 2H) |
| $^{19}$F-NMR(reference: CFCl$_3$), δ(ppm) | |
| –74.57 | (d, J=6.4Hz) |
| $[\alpha]_D^{25}$=–12.4°(c(concentration)=1.04; solvent: chloroform) | |
| mass analysis m/e(M$^+$) | |
| calculated for $C_{30}H_{43}F_3O_4N_2Si$ | 580.2944 |
| found | 580.2991 |

EXAMPLE 15

Synthesis of (2R,5R,6R)-tetrahydro-6-trifluoromethyl-2-[trans-4-(4'-hexyloxy-1'-phenyl)cyclohexane-1-carbonyloxy]-5-tert-butyl dimethylsiloxypyran

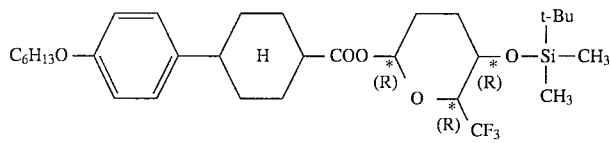

The same procedures as those in Example 9 were conducted by using 0.69 g (2.4 mmol) of trans-4-(4'-hexyloxy-1'-phenyl)cyclohexane-1carboxylic acid chloride and 0.60 g (2.0 mmol) of (5R,6R)-tetrahydro-5-tert-butyldimethylsiloxy-6-trifluoromethyl-2-hydroxypyran obtained by the same procedures as those in Reference Example 1, and 0.53 g (1.0 mmol) of the target compound (2R,5R,6R)-tetrahydro-6-trifluoromethyl-2-[trans-4-(4'-hexyloxy-1'-phenyl)cyclohexane-1-carbonyloxy]-5-tert-butyldimethylsiloxypyran was obtained.

Physical properties of the compound obtained are shown in the following.

Molecular formula: $C_{31}H_{49}F_3O_5Si$

| $^1$H-NMR, $\delta$(ppm) | |
|---|---|
| 0.07 | (s, 3H) |
| 0.08 | (s, 3H) |
| 0.83–1.04 | (m, 12H) |
| 1.27–1.83 | (m, 16H) |
| 1.88–2.40 | (m, 6H) |
| 3.75–3.89 | (m, 2H) |
| 3.92 | (t, J=6.6Hz, 2H) |
| 5.82 | (dd, J=2.5, 7.7Hz, 1H) |
| 6.82 | (d, J=8.6Hz, 2H) |
| 7.09 | (d, J=8.7Hz, 2H) |
| $^{19}$F-NMR(reference: CFCl$_3$), $\delta$(ppm) | |
| −74.60 | (d, J=6.5Hz) |
| $[\alpha]_D^{27}$=−8.0°(c(concentration)=1.01; solvent: chloroform) | |
| mass analysis m/e(M$^+$) | |
| calculated for $C_{31}H_{49}F_3O_5Si$ | 586.3301 |
| found | 586.3304 |

EXAMPLE 16

Synthesis of (2R,5R,6R)-tetrahydro-6-trifluoromethyl-2-(4-decyloxyphenyl-1-carbonyloxy)-5-tert-butyldimethylsiloxypyran

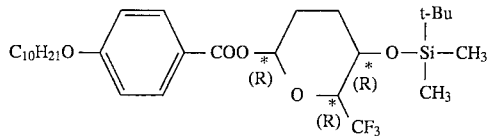

The same procedures as those in Example 9 were conducted by using 0.71 g (2.4 mmol) of 4-decyloxybenzoic acid chloride and 0.60 g (2.0 mmol) of (5R,6R)-tetrahydro-5-tert-butyldimethylsiloxy-6-trifluoromethyl-2-hydroxypyran obtained by the same procedures as those in Reference Example 1, and 0.66 g (1.2 mmol) of the target compound (2R, R,6R)-tetrahydro-6-trifluoromethyl-2-(4-decyloxyphenyl-1-carbonyloxy)-5-tert-butyldimethylsiloxypyran was obtained.

Physical properties of the compound obtained are shown in the following.

Molecular formula: $C_{29}H_{47}F_3O_5Si$

| $^1$H-NMR, $\delta$(ppm) | |
|---|---|
| 0.10 | (s, 3H) |
| 0.11 | (s, 3H) |
| 0.83–0.97 | (m, 12H) |
| 1.16–1.52 | (m, 14H) |
| 1.64–2.24 | (m, 6H) |
| 3.82–3.97 | (m, 2H) |
| 4.00 | (t, J=6.6Hz, 2H) |
| 6.03 | (dd, J=2.4, 7.9Hz, 1H) |
| 6.90 | (d, J=8.9Hz, 2H) |
| 8.00 | (d, J=8.9Hz, 2H) |
| $^{19}$F-NMR(reference: CFCl$_3$), $\delta$(ppm) | |
| −74.57 | (d, J=6.4Hz) |
| $[\alpha]_D^{25}$=−16.6°(c(concentration)=1.02; solvent: chloroform) | |

EXAMPLE 17

Host liquid crystal A made from a mixture of equal amounts (25% by weight each) of the following compounds was prepared. A liquid crystal composition was prepared by mixing the optically active tetrahydropyran derivative prepared in Example 1 to this host liquid crystal in an amount of 2% by weight.

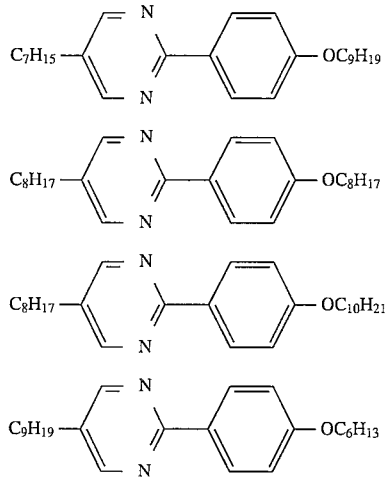

The phase transition temperatures of the liquid crystal obtained were as following:

$$SmC^* \xrightarrow{52°C.} SmA \xrightarrow{64°C.} N^* \xrightarrow{69°C.} Iso$$

SmC*: ferroelectric chiral smectic C phase
SmA: smectic A phase
N*: chiral nematic phase
Iso: isotropic liquid state This liquid crystal composition was injected at an isotropic phase into a liquid crystal cell of 2.0 μm gap having alignment films of polyimide which had been treated with the parallel rubbing. The liquid crystal device was cooled slowly and aligned. The liquid crystal device had a response time ($\tau_{0-90}$) of 92 μseconds under application of a rectangular wave voltage of $V_{pp}$=20 V at 30° C. The response time was obtained as the time in which the intensity of the transmitted light changes from 0 to 90% under a cross nicol. The liquid crystal device also had a spontaneous polarization of 8.3 nC/cm² measured by the triangular wave method.

EXAMPLE 18

The optically active tetrahydropyran derivative prepared in Example 2 was mixed with host liquid crystal A obtained in Example 17 in an amount of 2% by weight, and a liquid crystal composition was prepared.

The phase transition temperatures of the liquid crystal composition obtained were as following:

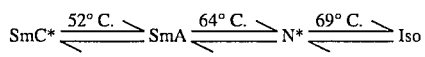

$$\text{SmC*} \xrightleftharpoons{52°\text{C.}} \text{SmA} \xrightleftharpoons{64°\text{C.}} \text{N*} \xrightleftharpoons{69°\text{C.}} \text{Iso}$$

This liquid crystal composition was injected at an isoptropic phase into a liquid crystal cell of 2.4 μm gap having alignment films of polyimide which had been treated with the parallel rubbing. The liquid crystal composition was cooled slowly and aligned. The liquid crystal device had a response time ($\tau_{0\text{-}90}$) of 94 μseconds under application of a rectangular wave voltage of $V_{pp}$=24 V at 30° C. The response time was obtained as the time in which the intensity of the transmitted light changes from 0 to 90% under a cross nicol. The liquid crystal device also had a spontaneous polarization of 6.8 nC/cm² measured by the triangular wave method.

EXAMPLE 19

The optically active tetrahydropyran derivative prepared in Example 2 was mixed with host liquid crystal A obtained in Example 17 in an amount of 5% by weight, and a liquid crystal composition was prepared.

The phase transition temperatures of the liquid crystal composition obtained were as following:

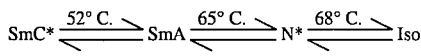

$$\text{SmC*} \xrightleftharpoons{52°\text{C.}} \text{SmA} \xrightleftharpoons{65°\text{C.}} \text{N*} \xrightleftharpoons{68°\text{C.}} \text{Iso}$$

This liquid crystal composition was injected at an isotropic phase into a liquid crystal cell of 2.4 μm gap having alignment films of polyimide which had been treated with the parallel rubbing. The liquid crystal composition was cooled slowly and aligned. The liquid crystal device had a response time ($\tau_{0\text{-}90}$) of 74 μseconds under application of a rectangular wave voltage of $V_{pp}$=24 V at 30° C. The response time was obtained as the time in which the intensity of the transmitted light changes from 0 to 90% under a cross nicol. The liquid crystal device also had a spontaneous polarization of 20.8 nC/cm² measured by the triangular wave method.

EXAMPLES 20 to 33

An optically active tetrahydropyran derivative prepared in one of Examples 3 to 16 was mixed with host liquid crystal A obtained in Example 17 in an amount of 2% by weight, and a liquid crystal composition was prepared. The phase transition temperatures of the liquid crystal composition obtained were measured. Results are shown in Table 1.

A liquid crystal device was prepared by using the liquid crystal composition prepared above by the same procedures as those described in Example 17, and the response time and the spontaneous polarization of the liquid crystal device were measured. Results are shown in Table 1.

TABLE 1

| Example No. | compound added to liquid crystal A Example No. | amount (% by wt.) | phase transition temperature (°C.) SmC* ⇌ SmA | ⇌ N* | ⇌ Iso | response time (μsec) | spontaneous polarization (nC/cm²) |
|---|---|---|---|---|---|---|---|
| 17 | 1 | 2 | 52 | 64 | 69 | 92 | 8.3 |
| 18 | 2 | 2 | 52 | 64 | 69 | 94 | 6.8 |
| 19 | 2 | 5 | 52 | 65 | 68 | 74 | 20.8 |
| 20 | 3 | 2 | 51 | 64 | 68 | 96 | 7.9 |
| 21 | 4 | 2 | 50 | 64 | 68 | 95 | 5.6 |
| 22 | 5 | 2 | 47 | 63 | 67 | 90 | 6.3 |
| 23 | 6 | 2 | 47 | 63 | 67 | 86 | 6.4 |
| 24 | 7 | 2 | 47 | 63 | 67 | 82 | 6.3 |
| 25 | 8 | 2 | 50 | 64 | 68 | 112 | 4.3 |
| 26 | 9 | 2 | 52 | 64 | 69 | 98 | 7.2 |
| 27 | 10 | 2 | 52 | 65 | 69 | 97 | 6.8 |
| 28 | 11 | 2 | 52 | 65 | 69 | 100 | 5.9 |
| 29 | 12 | 2 | 51 | 65 | 69 | 110 | 4.8 |
| 30 | 13 | 2 | 49 | 65 | 68 | 94 | 5.7 |
| 31 | 14 | 2 | 50 | 64 | 69 | 98 | 5.4 |
| 32 | 15 | 2 | 50 | 62 | 67 | 129 | 5.3 |
| 33 | 16 | 2 | 51 | 62 | 67 | 124 | 5.3 |

What is claimed is:

1. An optically active tetrahydropyran derivative represented by formula (I) or (I') or (I'') or (I''')

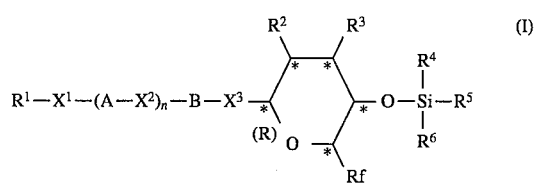

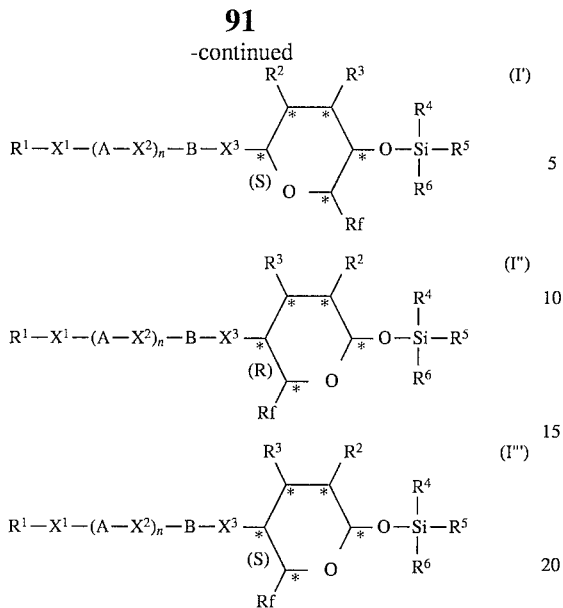

wherein Rf represents a fluoroalkyl group having 1 or 2 carbon atoms; $R^1$ represents a linear or branched alkyl group having 3 to 20 carbon atoms; $R^2$ and $R^3$ each independently represent a hydrogen atom, a linear or branched alkyl group having 1 to 15 carbon atoms, an alkenyl group having 2 to 15 carbon atoms, or an aralkyl group having 7 to 10 carbon atoms; $R^4$, $R^5$, and $R^6$ each independently represent a hydrogen atom, a linear or branched alkyl group having 1 to 15 carbon atoms, an alkenyl group having 2 to 15 carbon atoms, an aryl group having 6 to 10 carbon atoms, or an aralkyl group having 7 to 10 carbon atoms; $X^1$ represents —COO—, —OCO—, —O—, or a single bond; $X^2$ represents —COO—, —OCO—, —CH$_2$O—, —OCH$_2$—, —C≡C—, or a single bond; $X^3$ represents —COO—, —CH$_2$O—, or —O—; Si represents a silicon atom; * denotes that the carbon atom having this mark is an asymmetric carbon atom; A and B each independently represent a substituted or unsubstituted group containing a six-membered ring; and n represents 0 or 1.

2. An optically active tetrahydropyran derivative according to claim 1, wherein A and B in general formula (I) or (I') or (I") or (I''') each independently represent one of the following groups:

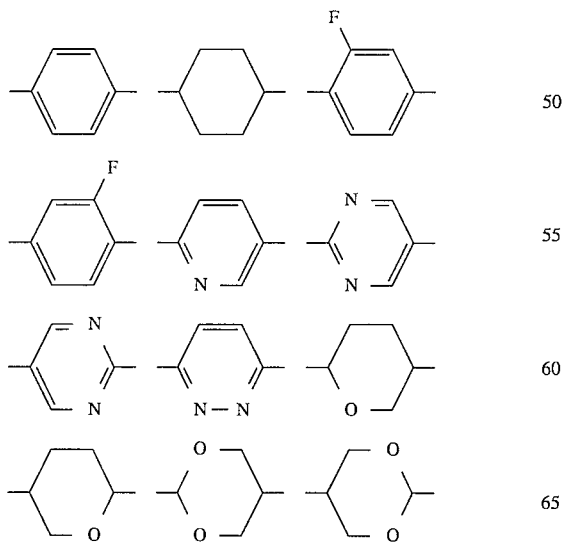

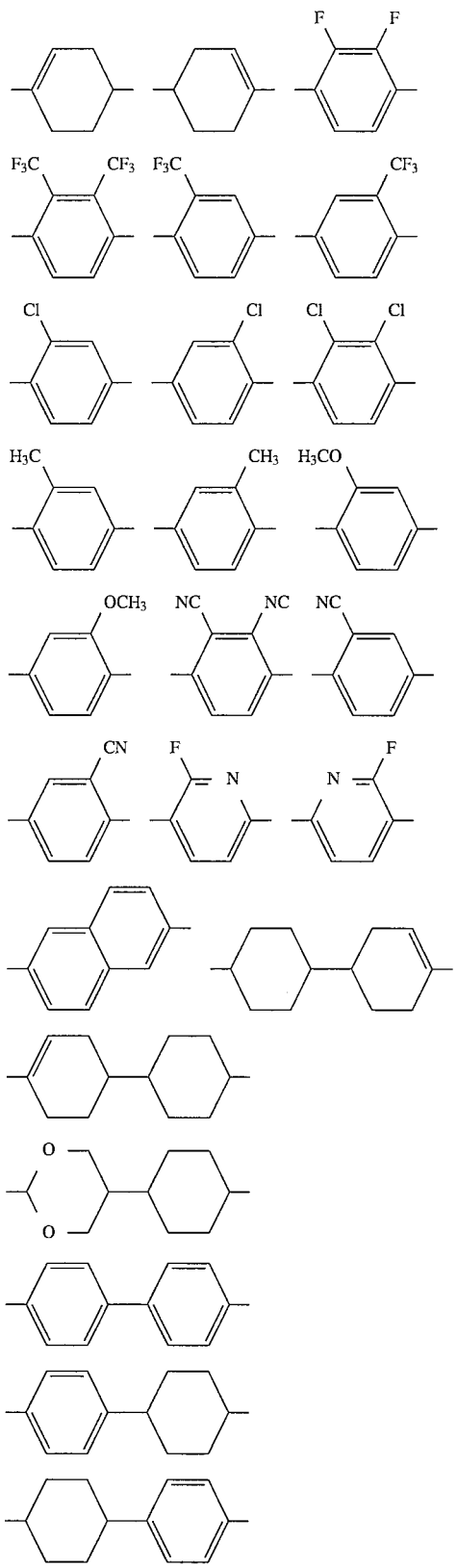

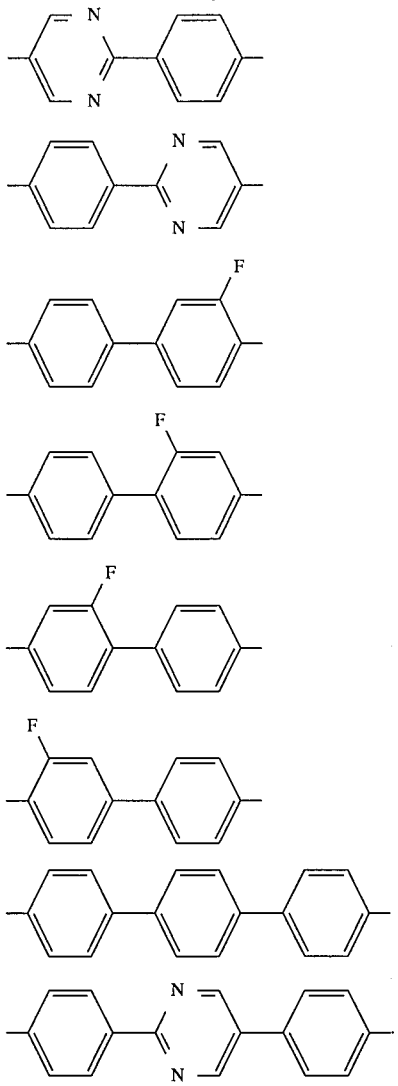

3. A liquid crystal composition comprising (a) at least one compound selected from the optically active tetrahydropyran derivatives described in claim 1; and (b) a compound or a mixture of compounds having a chiral smectic C phase (SmC*) which is different from the optically active tetrahydropyran derivative selected in (a); and/or (c) a compound or a mixture of compounds having a smectic C phase (SmC) which is different from the optically active tetrahydropyran derivative selected in (a).

4. A liquid crystal device comprising a pair of electrode plates and at least one of the optically active tetrahydropyran derivatives described in claim 1 wherein said at least one tetrahydropyran derivative is arranged between the pair of electrode plates.

5. A liquid crystal composition comprising (a) at least one compound selected from the optically active tetrahydropyran derivatives described in claim 2;

(b) a compound or a mixture of compounds having a chiral smectic C phase (SmC*) which is different from the optically active tetrahydropyran derivative selected in (a); and/or (c) a compound or a mixture of compounds having a smectic C phase (SmC) which is different from the optically active tetrahydropyran derivative selected in (a).

6. A liquid crystal device comprising a pair of electrode plates and at least one of the optically active tetrahydropyran derivative described in claim 2, wherein said at least one tetrahydropyran derivative is arranged between the pair of electrode plates.

* * * * *